(12) United States Patent
Bailey et al.

(10) Patent No.: US 10,039,505 B2
(45) Date of Patent: Aug. 7, 2018

(54) ANATOMICAL IMAGING SYSTEM HAVING FIXED GANTRY AND ROTATING DISC, WITH ADJUSTABLE ANGLE OF TILT AND INCREASED STRUCTURAL INTEGRITY, AND WITH IMPROVED POWER TRANSMISSION AND POSITION SENSING

(71) Applicant: Samsung Electronics Co., Ltd., Gyeonggi-do (KR)

(72) Inventors: Eric Bailey, North Hampton, NH (US); Andrew Tybinkowski, Boxford, MA (US); Pil Yong Oh, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 189 days.

(21) Appl. No.: 14/805,065

(22) Filed: Jul. 21, 2015

(65) Prior Publication Data

US 2016/0022232 A1  Jan. 28, 2016

Related U.S. Application Data

(60) Provisional application No. 62/027,433, filed on Jul. 22, 2014, provisional application No. 62/027,472, filed on Jul. 22, 2014, provisional application No. 62/027,444, filed on Jul. 22, 2014, provisional application No. 62/027,420, filed on Jul. 22, 2014.

(51) Int. Cl.
*A61B 6/03* (2006.01)
*A61B 6/00* (2006.01)
*A61B 6/10* (2006.01)

(52) U.S. Cl.
CPC ............. *A61B 6/035* (2013.01); *A61B 6/032* (2013.01); *A61B 6/4447* (2013.01); *A61B 6/56* (2013.01); *A61B 6/105* (2013.01)

(58) Field of Classification Search
CPC ......... A61B 6/032; A61B 6/035; A61B 6/105; A61B 6/4447; A61B 6/56
USPC ..................... 378/15, 17, 196–198
See application file for complete search history.

(56) References Cited

U.S. PATENT DOCUMENTS

| 4,190,773 A | * | 2/1980 | Braden | A61B 6/032 378/10 |
| 4,266,135 A | * | 5/1981 | Kuwik | A61B 6/032 378/147 |
| 4,304,999 A | * | 12/1981 | Richey | A61B 6/032 378/147 |
| 4,817,119 A | * | 3/1989 | Ledley | A61B 6/032 378/19 |

(Continued)

FOREIGN PATENT DOCUMENTS

| KR | 10-0368839 | 9/2002 |
| KR | 10-2013-0131390 | 12/2013 |
| WO | WO 2012/161383 | 11/2012 |

OTHER PUBLICATIONS

Notice of ALlowance issued by Korean Intellectual Property Office in Korean Patent Application No. 10-2015-0103865, dated Jan. 9, 2017 (with partial translation).

(Continued)

*Primary Examiner* — Allen C. Ho
(74) *Attorney, Agent, or Firm* — Pandiscio & Pandiscio

(57) ABSTRACT

An anatomical imaging system of the sort having a fixed gantry and a rotating disc, with an adjustable angle of tilt and increased structural integrity, and with improved power transmission and position sensing.

16 Claims, 29 Drawing Sheets

(56) References Cited

U.S. PATENT DOCUMENTS

| | | | |
|---|---|---|---|
| 5,109,397 A * | 4/1992 | Gordon | A61B 6/035 378/20 |
| 5,448,607 A * | 9/1995 | McKenna | A61B 6/035 378/17 |
| 5,448,608 A * | 9/1995 | Swain | A61B 6/035 378/15 |
| 5,999,587 A * | 12/1999 | Ning | A61B 6/4447 378/4 |
| 6,337,894 B1 * | 1/2002 | Tybinkowski | F16C 19/183 378/15 |
| 6,400,791 B1 * | 6/2002 | Schwarz | A61B 6/0457 378/15 |
| 6,452,998 B2 | 9/2002 | Tybinkowski et al. | |
| 6,519,312 B1 * | 2/2003 | Tybinkowski | A61B 6/035 378/15 |
| 6,553,091 B2 * | 4/2003 | Takanashi | A61B 6/035 378/15 |
| 6,580,777 B1 * | 6/2003 | Ueki | A61B 6/032 378/15 |
| 6,590,953 B2 * | 7/2003 | Suzuki | A61B 6/035 310/211 |
| 6,721,388 B2 | 4/2004 | Tybinkowski et al. | |
| 6,751,283 B2 * | 6/2004 | van de Haar | A61B 6/032 378/15 |
| 6,831,961 B1 * | 12/2004 | Tybinkowski | A61B 6/032 250/363.04 |
| 6,890,100 B2 * | 5/2005 | Reznicek | A61B 6/035 378/15 |
| 7,175,347 B2 * | 2/2007 | Tybinkowski | A61B 6/032 378/196 |
| 7,265,356 B2 * | 9/2007 | Pelizzari | A61N 5/1049 250/370.09 |
| 7,848,488 B2 * | 12/2010 | Mansfield | A61N 5/10 378/197 |
| 8,118,488 B2 * | 2/2012 | Gregerson | A61B 5/0555 378/196 |
| 8,128,286 B2 | 3/2012 | Shindo | |
| 8,170,175 B2 * | 5/2012 | Kasuya | A61B 6/035 378/15 |
| 8,270,563 B2 | 9/2012 | Harris et al. | |
| 8,299,670 B2 * | 10/2012 | Krumme | A61B 6/035 310/90 |
| 8,693,621 B2 * | 4/2014 | Thran | A61B 6/4021 378/17 |
| 8,753,009 B2 * | 6/2014 | Gregerson | A61B 6/035 378/196 |
| 8,770,839 B2 * | 7/2014 | Gregerson | A61B 6/4488 378/193 |
| 8,781,061 B2 * | 7/2014 | Mochitate | A61B 6/035 378/189 |
| 8,807,833 B2 * | 8/2014 | Sharpless | A61B 6/035 378/197 |
| 8,985,852 B2 * | 3/2015 | Theiss | A61B 6/035 378/197 |
| 9,125,613 B2 * | 9/2015 | Gregerson | A61B 6/4488 |
| 9,247,917 B2 * | 2/2016 | Kodaira | A61B 6/032 |
| 9,254,108 B2 * | 2/2016 | Maki | A61B 6/4435 |
| 9,351,693 B2 * | 5/2016 | Sharpless | A61B 6/035 |
| 9,526,461 B2 * | 12/2016 | Gregerson | A61B 6/032 |
| 9,750,472 B2 * | 9/2017 | Liu | A61B 6/4417 |
| 2008/0211322 A1 | 9/2008 | Heinrich et al. | |
| 2010/0034492 A1 | 2/2010 | Krumme | |
| 2010/0303197 A1 | 12/2010 | Kasuya | |
| 2012/0032084 A1 | 2/2012 | Sapp et al. | |

OTHER PUBLICATIONS

Official Action issued by Korean Intellectual Property Office, dated Sep. 13, 2016 (with partial translation).

* cited by examiner

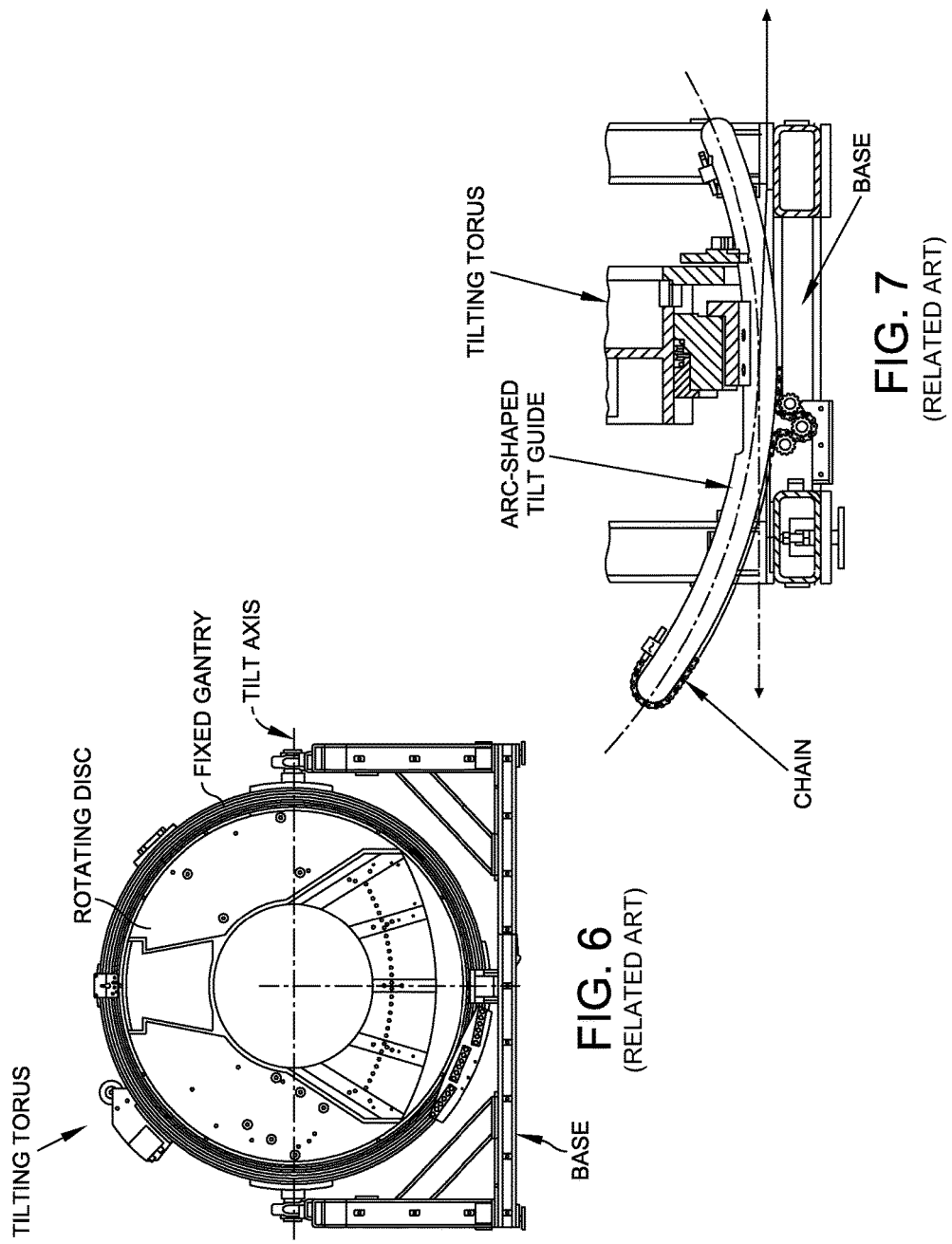

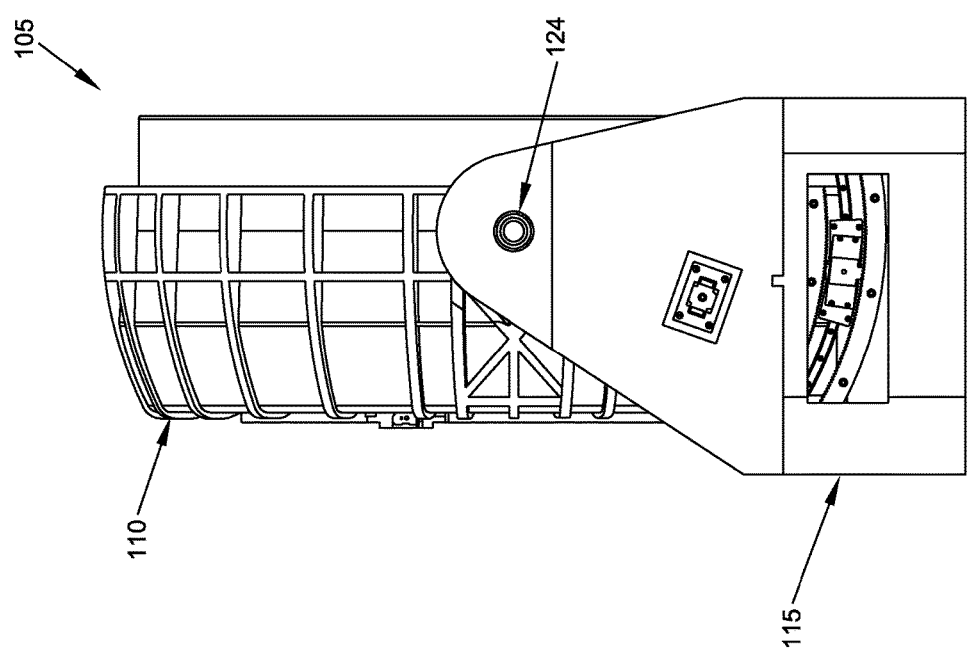

ANATOMICAL IMAGING SYSTEM HAVING FIXED GANTRY AND ROTATING DISC, WITH ADJUSTABLE ANGLE OF TILT AND INCREASED STRUCTURAL INTEGRITY, AND WITH IMPROVED POWER TRANSMISSION AND POSITION SENSING

REFERENCE TO PENDING PRIOR PATENT APPLICATIONS

This patent application:

(i) claims benefit of prior U.S. Provisional Patent Application Ser. No. 62/027,433, filed Jul. 22, 2014 by Neurologica Corp. and Eric Bailey et al. for ANATOMICAL IMAGING SYSTEM WITH IMPROVED ROTATING SLIP RING;

(ii) claims benefit of prior U.S. Provisional Patent Application Ser. No. 62/027,472, filed Jul. 22, 2014 by Neurologica Corp. and Eric Bailey et al. for ANATOMICAL IMAGING SYSTEM WITH TILTING TORUS, TILT BRAKE AND FAIL-SAFE BRAKE;

(iii) claims benefit of prior U.S. Provisional Patent Application Ser. No. 62/027,444, filed Jul. 22, 2014 by Neurologica Corp. and Eric Bailey et al. for ANATOMICAL IMAGING SYSTEM WITH IMPROVED POSITION SENSOR; and (iv) claims benefit of prior U.S. Provisional Patent Application Ser. No. 62/027,420, filed Jul. 22, 2014 by Neurologica Corp. and Eric Bailey et al. for ANATOMICAL IMAGING SYSTEM WITH FIXED CUP-SHAPED GANTRY AND ROTATING CUP-SHAPED DISC.

The four (4) above-identified patent applications are hereby incorporated herein by reference.

FIELD OF THE INVENTION

This invention relates to imaging systems in general, and more particularly to anatomical imaging systems.

BACKGROUND OF THE INVENTION

In many situations it can be desirable to image the interior of opaque objects. By way of example but not limitation, in the medical field, it can be desirable to image the interior of a patient's body so as to allow viewing of internal structures without physically penetrating the skin.

Computerized Tomography (CT) has emerged as a key imaging modality in the medical field. CT imaging systems generally operate by directing X-rays into the body from a variety of positions, detecting the X-rays passing through the body, and then processing the detected X-rays so as to build a three-dimensional (3D) data set and a 3D computer model of the patient's anatomy. The 3D data set and 3D computer model can then be visualized so as to provide images (e.g., slice images, 3D computer images, etc.) of the patient's anatomy.

By way of example but not limitation, and looking now at FIGS. 1 and 2, there is shown an exemplary CT imaging system 5. CT imaging system 5 generally comprises a torus 10 which is supported by a base 15. A center opening 20 is formed in torus 10. Center opening 20 receives the patient anatomy which is to be scanned.

Looking next at FIG. 3, torus 10 generally comprises a fixed gantry 22, a rotating disc 23, an X-ray tube assembly 25 and an X-ray detector assembly 30. More particularly, fixed gantry 22 is disposed concentrically about center opening 20. Rotating disc 23 is rotatably mounted to fixed gantry 22. X-ray tube assembly 25 and X-ray detector assembly 30 are mounted to rotating disc 23 in diametrically-opposing relation, such that an X-ray beam 40 (generated by X-ray tube assembly 25 and detected by X-ray detector assembly 30) is passed through the patient anatomy disposed in center opening 20. Inasmuch as X-ray tube assembly 25 and X-ray detector assembly 30 are mounted on rotating disc 23 so that they are rotated concentrically about center opening 20, X-ray beam 40 will be passed through the patient's anatomy along a full range of radial positions, so as to enable CT imaging system 5 to create a "slice" image of the anatomy penetrated by the X-ray beam 40. Furthermore, by moving the patient and CT imaging system 5 relative to one another during scanning, a series of slice images can be acquired, and thereafter appropriately processed, so as to create a 3D data set of the scanned anatomy and a 3D computer model of the scanned anatomy. In practice, it is common to configure X-ray detector assembly 30 so that multiple slices of images (e.g., 8 slices, 16 slices, 32 slices, etc.) may be acquired with each rotation of rotating disc 23, whereby to speed up the acquisition of scan data.

In practice, it is now common to effect helical scanning of the patient's anatomy so as to generate a 3D data set of the scanned anatomy, which can then be processed to build a 3D computer model of the scanned anatomy. The 3D data set and 3D computer model can then be visualized so as to provide images (e.g., slice images, 3D computer images, etc.) of the patient's anatomy.

The various electronic hardware and software for controlling the operation of rotating disc 23, X-ray tube assembly 25 and X-ray detector assembly 30, as well as for processing the acquired scan data so as to generate the desired slice images, 3D data set and 3D computer model, may be of the sort well known in the art and may be located in torus 10 and/or base 15.

In many cases CT imaging system 5 is intended to be stationary, in which case base 15 of CT imaging system 5 is set in a fixed position on the floor of a room and a special motorized movable bed is provided to move the patient relative to CT imaging system 5 during scanning. More particularly, with a stationary CT imaging system 5, the patient is brought to the location of CT imaging system 5, the patient is placed on the motorized movable bed, and then the motorized movable bed is used to move the patient relative to CT imaging system 5 (i.e., to advance the patient into center opening 20 of CT imaging system 5) so that some or all of the length of the patient may be scanned by CT imaging system 5.

In other cases CT imaging system 5 is intended to be mobile so that the CT imaging system 5 may be brought to the patient and the patient scanned at the patient's current location, rather than requiring that the patient be transported to the location of the CT imaging system 5. Scanning the patient with a mobile CT imaging system 5 can be highly advantageous, since it can reduce delays in patient scanning (e.g., the patient can be scanned in an emergency room rather than waiting to be transported to the radiology department) and/or it can allow the patient to be scanned without requiring movement of the patient (e.g., the patient can be scanned at their bedside in an intensive care unit, "ICU"). To this end, and looking now at FIGS. 4 and 5, base 15 may comprise a transport assembly 50 for (i) moving mobile CT imaging system 5 to the patient prior to scanning and (ii) moving the CT imaging system 5 relative to the patient during scanning. More particularly, transport assembly 50 preferably comprises (i) a gross movement mechanism 55 for moving CT imaging system 5 relatively quickly across room distances, so that the CT imaging system 5 can be quickly and easily brought to the bedside of the patient, such that the patient can be scanned at their bedside without needing to be moved to a radiology department, and (ii) a fine movement mechanism 60 for moving the CT imaging system precisely, relative to the patient, during scanning so that the patient can be scanned on their bed or gurney without needing to be moved onto a special motorized movable bed.

In one preferred form of the invention, gross movement mechanism 55 preferably comprises a plurality of free-rolling casters 62, and fine movement mechanism 60 preferably comprises a plurality of centipede belt drives 63 (which can be configured for either stepped or continuous motion, whereby to provide either stepped or continuous scanning of the patient). Hydraulic apparatus 65 permits either gross movement mechanism 55 or fine movement mechanism 60 to be engaged with the floor, whereby to facilitate appropriate movement of mobile CT imaging system 5. Thus, with a mobile CT imaging system 5, the mobile CT imaging system 5 may be pre-positioned in an "out of the way" location (e.g., in an unused corner of an emergency room) and then, when a patient requires scanning, the patient may be quickly and easily scanned at their bedside, by simply moving the mobile CT imaging system 5 to the patient's bedside on gross movement mechanism 55 (e.g., casters 62), and thereafter moving the mobile CT imaging system 5 during scanning on fine movement mechanism 60 (e.g., centipede belt drives 63).

Adjusting the Angle of the CT Scan Relative to the Body of the Patient

It has also been recognized that it can sometimes be useful to adjust the angle of the CT scan relative to the body of the patient, whereby to create a CT image which is set at an angle that is not perpendicular to the longitudinal axis of the patient's body. By way of example but not limitation, it can sometimes be desirable to obtain a CT image of the anatomy at a non-perpendicular angle to the longitudinal axis of the patient, whereby to image a particular feature. This may be achieved by tilting the patient at an angle to the scanning axis of the CT imaging system 5 (e.g., by using a tilting table so as to tilt the patient relative to the scanning axis of the CT imaging system 5). However, tilting the patient relative to the scanning axis of the CT imaging system 5 can be undesirable in many situations (e.g., where the patient's condition makes it unsafe or undesirable to tilt the patient in a desired way). In such circumstances, it may be desirable to instead tilt the torus 10 of the CT imaging system 5 relative to the patient in order to obtain the desired CT image.

One approach to tilting the torus 10 of a CT imaging system 5 relative to the patient is to attach a pair of large, arc-shaped tilt guides to the torus 10 of the CT imaging system 5, and to run a chain over the arc-shaped tilt guides. The chain is, in turn, attached to a gear and motor so that rotating the chain causes the torus 10 to tilt relative to the base 15 of the CT imaging system 5. See, for example, FIGS. 6 and 7, which illustrate such an apparatus.

However, it has been recognized that the provision and use of large arc-shaped tilt guides significantly enlarges the profile of the CT imaging system 5 (i.e., by extending outwardly from the base of the CT imaging system 5) and can present a hazardous obstruction for personnel working around the CT imaging system 5.

It has also been recognized that where the torus 10 of the CT imaging system 5 is to be tilted relative to the patient, it may be desirable to provide a brake or other means for locking the tilted torus 10 in a particular tilted position.

And it has been recognized that where the torus 10 of the CT imaging system 5 is to be tilted relative to the patient, it may also be desirable to provide an emergency braking system so as to prevent the torus 10 (which is typically quite large) from "falling" or "swinging" if power to the CT imaging system 5 should be interrupted and the tilting system should fail, since such unexpected movement of the torus 10 could injure personnel operating the CT imaging system 5 and/or a patient being scanned by the CT imaging system 5.

Thus there is a need for novel apparatus for tilting the torus 10 of a CT imaging system 5 which minimizes the profile of the CT imaging system 5 while maximizing the degree of tilt available for scanning. There is also a need for a novel brake or other means for locking the tilted torus 10 in a particular tilted position. There is also a need for a novel emergency brake for maintaining the tilt of the torus 10 in the event that power to the CT imaging system 5 is interrupted.

Increasing the Structural Integrity of the Rotating Disc and the Associated Fixed Gantry It has been recognized that substantial advantages can be obtained if the time required to scan the patient can be reduced. For one thing, patients sometimes move during the scan, which can result in degraded scan images. A faster scan time means that there is a reduced possibility that the patient will move mid-scan. For another thing, some patient anatomy is normally in motion, e.g., a beating heart. A faster scan time can make it possible to "freeze" the moving anatomy so as to allow imaging of the moving anatomy.

In general, there are two ways to reduce the time required to scan the patient. First, the X-ray detector assembly 30 can be configured to acquire more slice images with each rotation of rotating disc 23, whereby to speed up the acquisition of image data. Thus, over time, so-called "8 slice machines", "16 slice machines", "32 slice machines", etc. have been developed. Second, the speed of rotation of the rotating disc 23 can be increased, whereby to speed up the acquisition of image data.

Unfortunately, increasing the number of slices acquired with each rotation of rotating disc 23, and/or increasing the speed of rotation of the rotating disc 23, can introduce design issues. For example, it may be desirable to increase the speed of rotation of rotating disc 23 (e.g., from 120 rpms to 240 rpms) so as to improve imaging speed. However, it has been found that increasing the speed of rotation of rotating disc 23 (e.g., from 120 rpms to 240 rpms) significantly increases the forces on rotating disc 23 and the components which are mounted to, and rotate with, rotating disc 23 (e.g., X-ray tube assembly 25 and X-ray detector assembly 30).

By way of example but not limitation, it has been found that as rotating disc 23 is rotated at higher speeds (e.g., 240 rpms) about center opening 20, greater centrifugal forces act on the components which are bolted to rotating disc 23, with the centrifugal forces being directed perpendicular to the direction in which the components are bolted to rotating disc 23 (i.e., the centrifugal forces are directed radially whereas the components are bolted to rotating disc 23 axially). As a result, the components mounted to rotating disc 23 may flex at their mounting points, which may in turn cause rotating disc 23 to flex. When this occurs, the alignment between components used for imaging (e.g., the alignment between X-ray tube assembly 25 and X-ray detector assembly 30) may be compromised, resulting in a degradation of image quality.

Thus there is also a need for a rotating disc (and associated fixed gantry) having greater structural integrity so as to provide increased stability for the components that are mounted to the rotating disc when the rotating disc is rotated at high speeds (e.g., 240 rpms). And there is a need for providing a new way for mounting components (e.g., X-ray tube assembly 25, X-ray detector assembly 30, etc.) to the rotating disc so as to mitigate the destabilizing effects of the centrifugal forces that are imposed on the components when the rotating disc is rotated.

SUMMARY OF THE INVENTION

These and other objects of the present invention are addressed by the provision and use of novel apparatus for selectively tilting the torus of a CT imaging system which minimizes the profile of the CT imaging system while also maximizing the degree to which the torus of the CT imaging system may be tilted.

The present invention also comprises the provision and use of novel apparatus for maintaining the tilt angle of the torus of a CT imaging system at a desired angle relative to the base of the CT imaging system after the torus has been tilted.

The present invention further comprises the provision and use of a novel fail-safe brake for preventing the torus of the CT imaging system from moving (i.e., tilting) relative to the base of the CT imaging system in the event that power to the CT imaging system is interrupted.

In one preferred form of the invention, there is provided apparatus for scanning a patient, said apparatus comprising:
  a base;
  a torus pivotally mounted to said base and carrying scanning apparatus;
  a planetary gear comprising a curved lower planet gear mounted to said base, a curved upper planet gear mounted to said torus, and a sun gear disposed between said curved lower planet gear and said curved upper planet gear; and
  a motor for rotating said sun gear;
  wherein rotation of said sun gear causes said sun gear to move longitudinally relative to said curved lower planet gear, and also causes said curved upper planet gear to move longitudinally relative to said sun gear, whereby to move said upper planet gear longitudinally relative to said lower planet gear;
  and further wherein longitudinal movement of said curved upper planet gear relative to said curved lower planet gear tilts said torus relative to said base.

In another preferred form of the invention, there is provided a method for scanning a patient, said method comprising:
  providing apparatus comprising:
  a base;
  a torus pivotally mounted to said base and carrying scanning apparatus;
  a planetary gear comprising a curved lower planet gear mounted to said base, a curved upper planet gear mounted to said torus, and a sun gear disposed between said curved lower planet gear and said curved upper planet gear; and
  a motor for rotating said sun gear;
  wherein rotation of said sun gear causes said sun gear to move longitudinally relative to said curved lower planet gear, and also causes said curved upper planet gear to move longitudinally relative to said sun gear, whereby to move said upper planet gear longitudinally relative to said lower planet gear;
  and further wherein longitudinal movement of said curved upper planet gear relative to said curved lower planet gear tilts said torus relative to said base;
  tilting said torus relative to said base by rotating said sun gear;
  positioning the object to be scanned within said torus; and
  scanning the object.

The objects of the present invention are also addressed by the provision and use of a novel CT imaging system comprising a fixed cup-shaped gantry and a rotating cup-shaped disc which is positioned within the fixed cup-shaped gantry, whereby to provide enhanced structural integrity so as to provide increased stability for the components that are mounted to the rotating cup-shaped disc when the rotating cup-shaped disc is rotated. The present invention also comprises the provision and use of a new way for mounting components (e.g., X-ray tube assembly 25, X-ray detector assembly 30, etc.) to the rotating disc so as to mitigate the destabilizing effects of the centrifugal forces that are imposed on the components when the rotating disc is rotated, i.e., by mounting the components to the interior side wall of the rotating cup-shaped disc.

In one preferred form of the invention, there is provided apparatus for scanning an object, said apparatus comprising:
  a fixed cup-shaped gantry;
  a rotating cup-shaped disc rotatably mounted at least partially within said fixed cup-shaped gantry;
  a detector element mounted to said rotating cup-shaped disc for detecting a signal; and
  a motor for rotating said rotating cup-shaped disc relative to said fixed cup-shaped gantry;
  wherein said detector element is configured to detect a signal while said motor is rotating said rotating cup-shaped disc relative to said fixed cup-shaped gantry.

In another preferred form of the invention, there is provided a method for scanning an object, said method comprising:
  providing apparatus comprising:
  a fixed cup-shaped gantry;
  a rotating cup-shaped disc rotatably mounted at least partially within said fixed cup-shaped gantry;
  a detector element mounted to said rotating cup-shaped disc for detecting a signal; and
  a motor for rotating said rotating cup-shaped disc relative to said fixed cup-shaped gantry;
  wherein said detector element is configured to detect a signal while said motor is rotating said rotating cup-shaped disc relative to said fixed cup-shaped gantry;
  positioning the object to be scanned within said rotating cup-shaped disc; and
  detecting the signal using said detector element as said rotating cup-shaped disc rotates relative to said fixed cup-shaped gantry so as to create a scan of the object.

The present invention further comprises the provision and use of a novel slip ring for providing electrical power to the rotating cup-shaped disc and/or to the components which are mounted to the rotating cup-shaped disc.

In one preferred form of the invention, there is provided apparatus for scanning an object, said apparatus comprising:
  a fixed gantry;
  a rotating disc rotatably mounted to said fixed gantry;
  a detector element mounted to said rotating disc for detecting a signal;

a motor for rotating said rotating disc relative to said fixed gantry; and a slip ring for transferring power and/or data between said fixed gantry and said rotating disc while said rotating disc is rotating, said slip ring being mounted to said rotating disc and comprising:

an outer surface and an inner surface;

at least one conductive strip extending circumferentially about said outer surface of said slip ring for transferring power and/or data between said fixed gantry and said slip ring; and at least one bus bar mounted to said inner surface of said slip ring for transferring power and/or data between said slip ring and said rotating disc, wherein said at least one bus bar is in communication with said at least one conductive strip, and further wherein at least a portion of said at least one bus bar extends along the axis of rotation of said rotating disc.

In another preferred form of the invention, there is provided a method for scanning an object, said method comprising:

a fixed gantry;

a rotating disc rotatably mounted to said fixed gantry;

a detector element mounted to said rotating disc for detecting a signal;

a motor for rotating said rotating disc relative to said fixed gantry; and a slip ring for transferring power and/or data between said fixed gantry and said rotating disc while said rotating disc is rotating, said slip ring being mounted to said rotating disc and comprising:

an outer surface and an inner surface;

at least one conductive strip extending circumferentially about said outer surface of said slip ring for transferring power and/or data between said fixed gantry and said slip ring; and at least one bus bar mounted to said inner surface of said slip ring for transferring power and/or data between said slip ring and said rotating disc, wherein said at least one bus bar is in communication with said at least one conductive strip, and further wherein at least a portion of said at least one bus bar extends along the axis of rotation of said rotating disc;

positioning the object to be scanned along the axis of rotation of said rotating disc; and detecting the signal as the rotating disc rotates relative to the fixed gantry so as to create a scan of the object.

And the present invention comprises the provision and use of a novel position sensor for determining the rotational disposition of the rotating cup-shaped disc relative to the fixed cup-shaped gantry in real-time.

In one preferred form of the invention, there is provided apparatus for scanning an object, said apparatus comprising:

a fixed gantry;

a rotating disc rotatably mounted to said fixed gantry;

a detector element mounted to said rotating disc for detecting a signal;

a motor for rotating said rotating disc relative to said fixed gantry; and a position sensor for determining the rotational disposition of said rotating disc relative to said fixed gantry, said position sensor comprising:

a fixed encoder reader mounted to said fixed gantry; and a rotating rotary encoder strip mounted to said rotating disc and extending circumferentially around said rotating disc;

wherein said fixed encoder reader is disposed adjacent to said rotating rotary encoder strip such that said fixed encoder reader can read said rotating rotary encoder strip so as to determine the rotational disposition of said rotating rotary encoder strip relative to said fixed encoder reader, and hence the rotational disposition of said rotating disc relative to said fixed gantry.

In another preferred form of the invention, there is provided a method for scanning an object, said method comprising:

providing apparatus comprising:

a fixed gantry;

a rotating disc rotatably mounted to said fixed gantry;

a detector element mounted to said rotating disc for detecting a signal;

a motor for rotating said rotating disc relative to said fixed gantry; and a position sensor for determining the rotational disposition of said rotating disc relative to said fixed gantry, said position sensor comprising:

a fixed encoder reader mounted to said fixed gantry; and a rotating rotary encoder strip mounted to said rotating disc and extending circumferentially around said rotating disc;

wherein said fixed encoder reader is disposed adjacent to said rotating rotary encoder strip such that said fixed encoder reader can read said rotating rotary encoder strip so as to determine the rotational disposition of said rotating rotary encoder strip relative to said fixed encoder reader, and hence the rotational disposition of said rotating disc relative to said fixed gantry.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIGS. 6 and 7 are schematic views showing related art apparatus for tilting the torus of a CT imaging system;

FIGS. 8-17 are schematic views showing a CT imaging system which incorporates a novel planetary gear for tilting the torus of the CT imaging system;

DETAILED DESCRIPTION OF THE PREFERRED EMBODIMENTS

Figure 1:
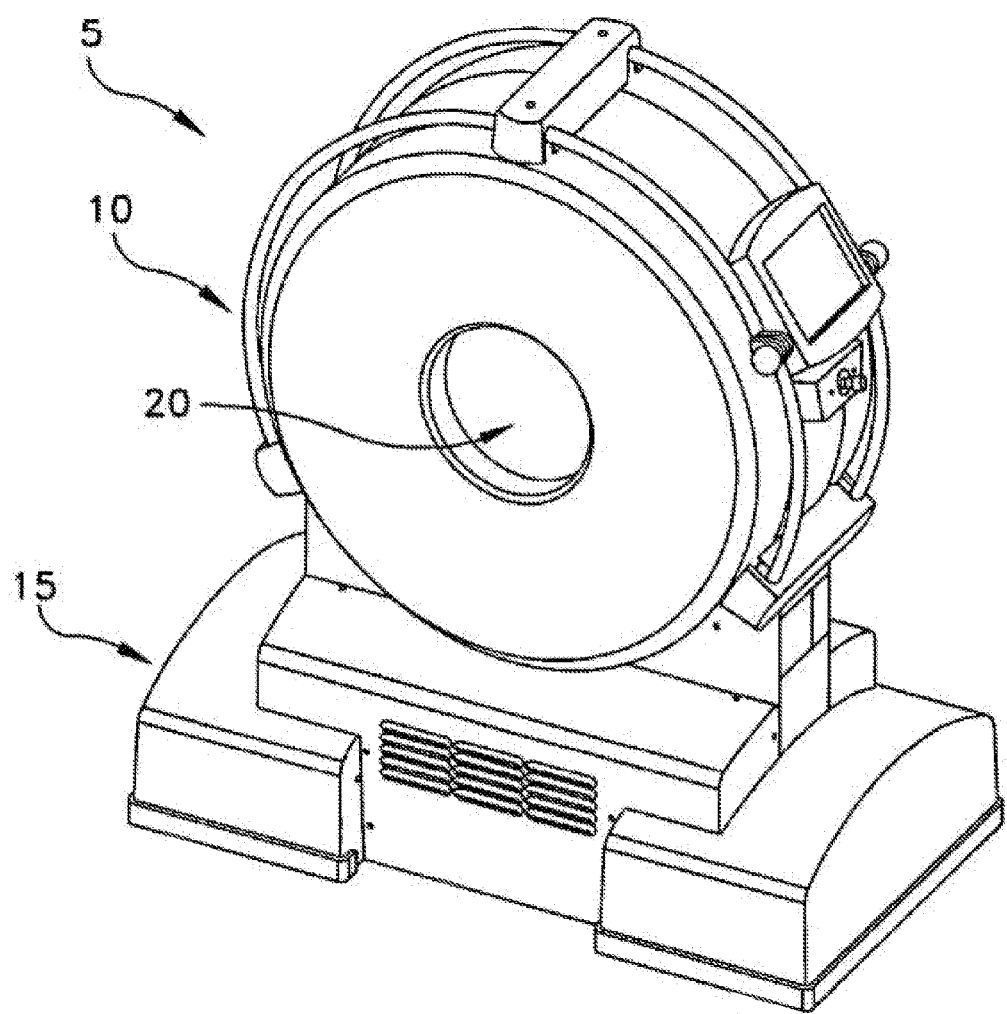
FIGS. 1 and 2 are schematic views showing the exterior of an exemplary CT imaging system.
Figure 2:
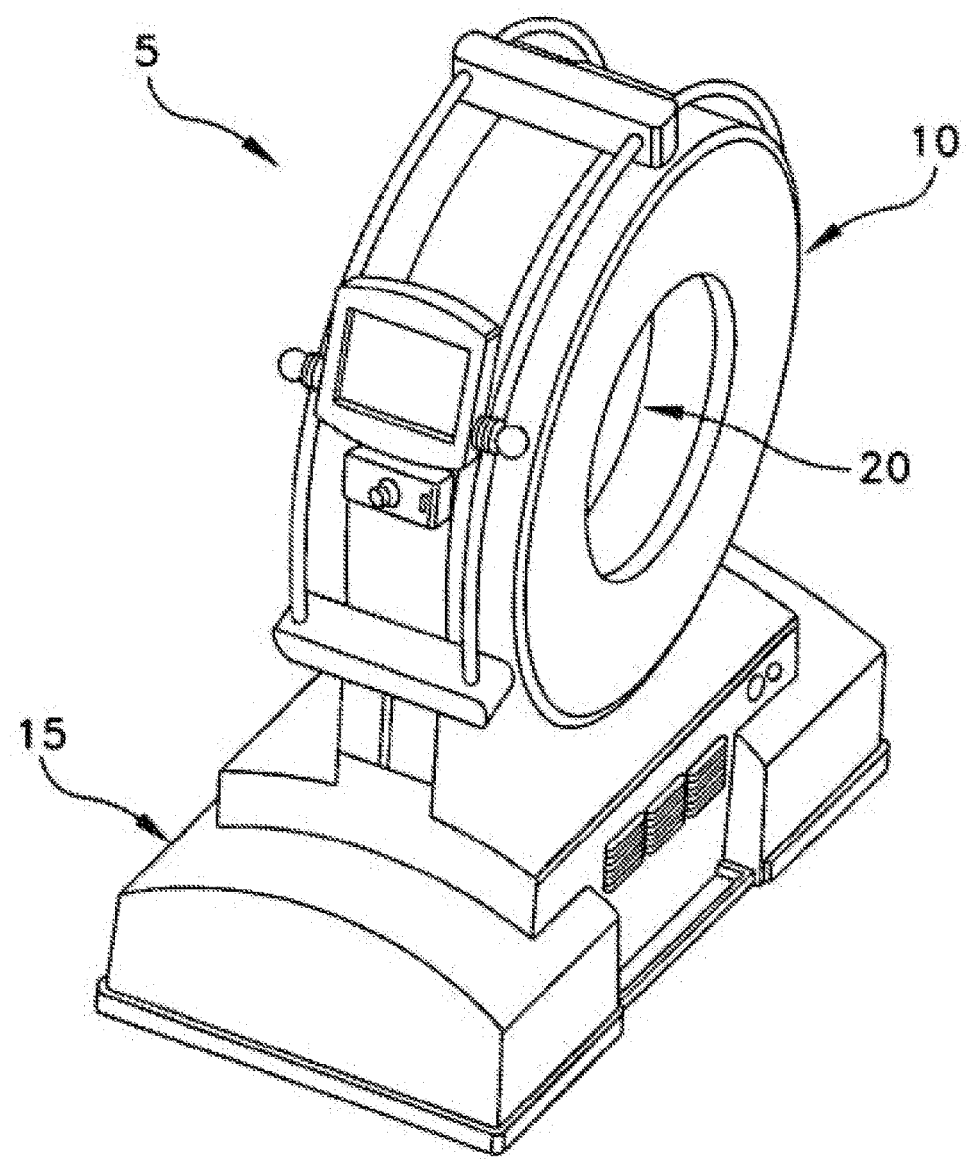
Figure 3:
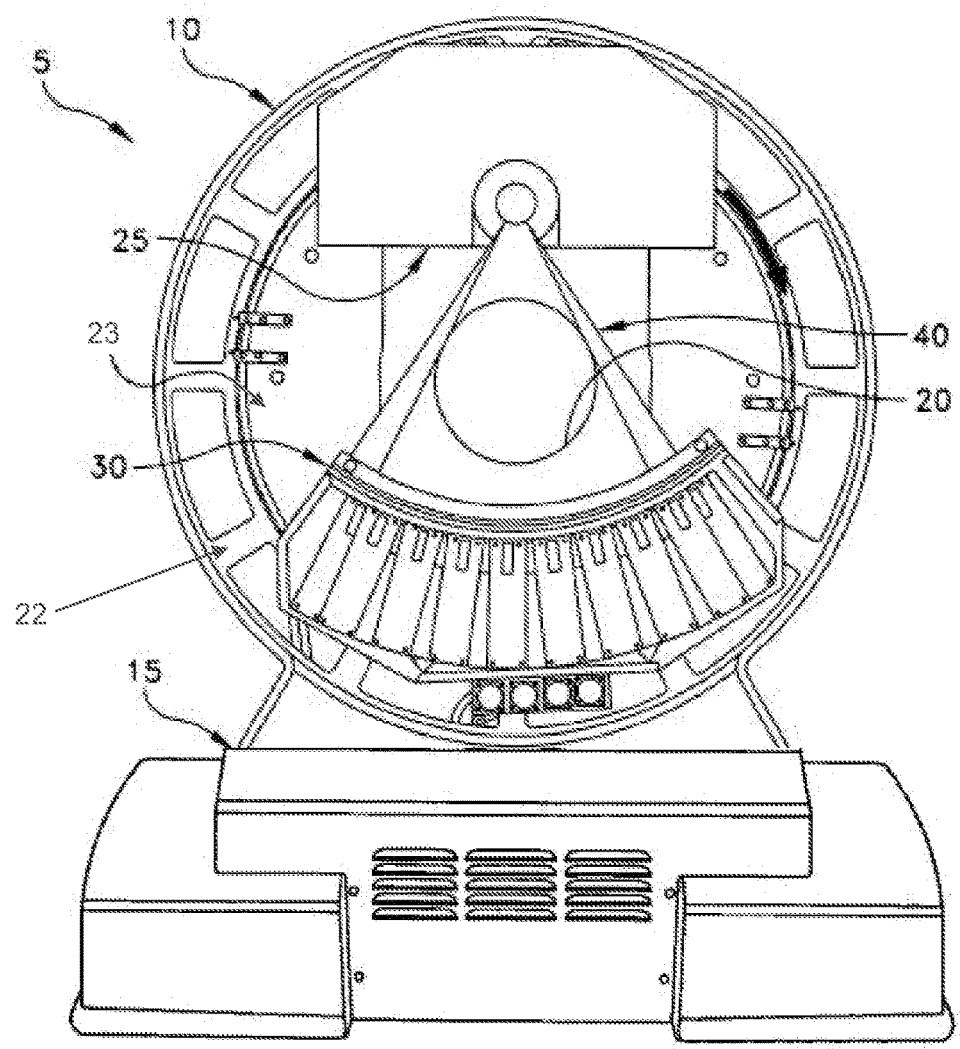
FIG. 3 is a schematic view showing various components in the torus of the exemplary CT imaging system shown in FIGS. 1 and 2.
Figure 4:
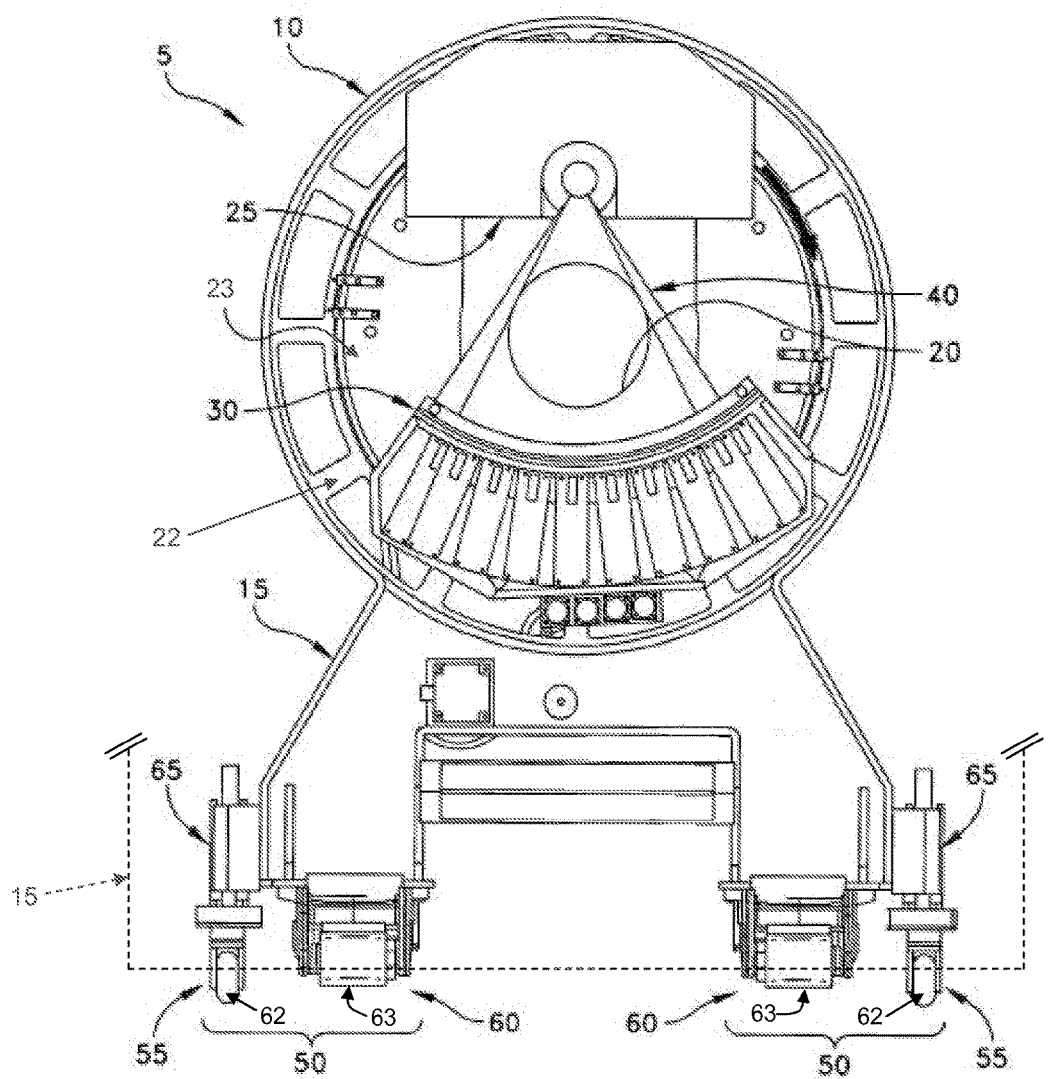
FIGS. 4 and 5 are schematic views showing an exemplary transport assembly for an exemplary CT imaging system.
Figure 5:
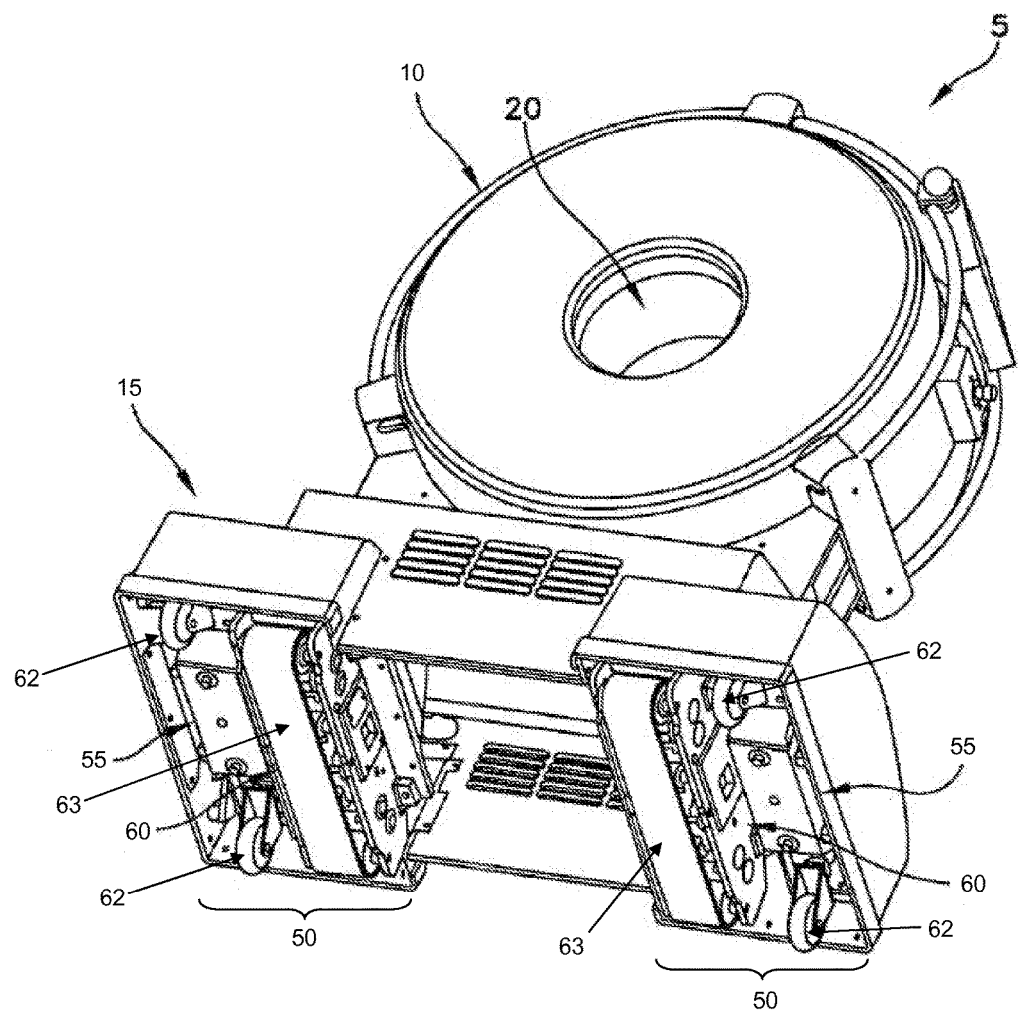
Figure 9:
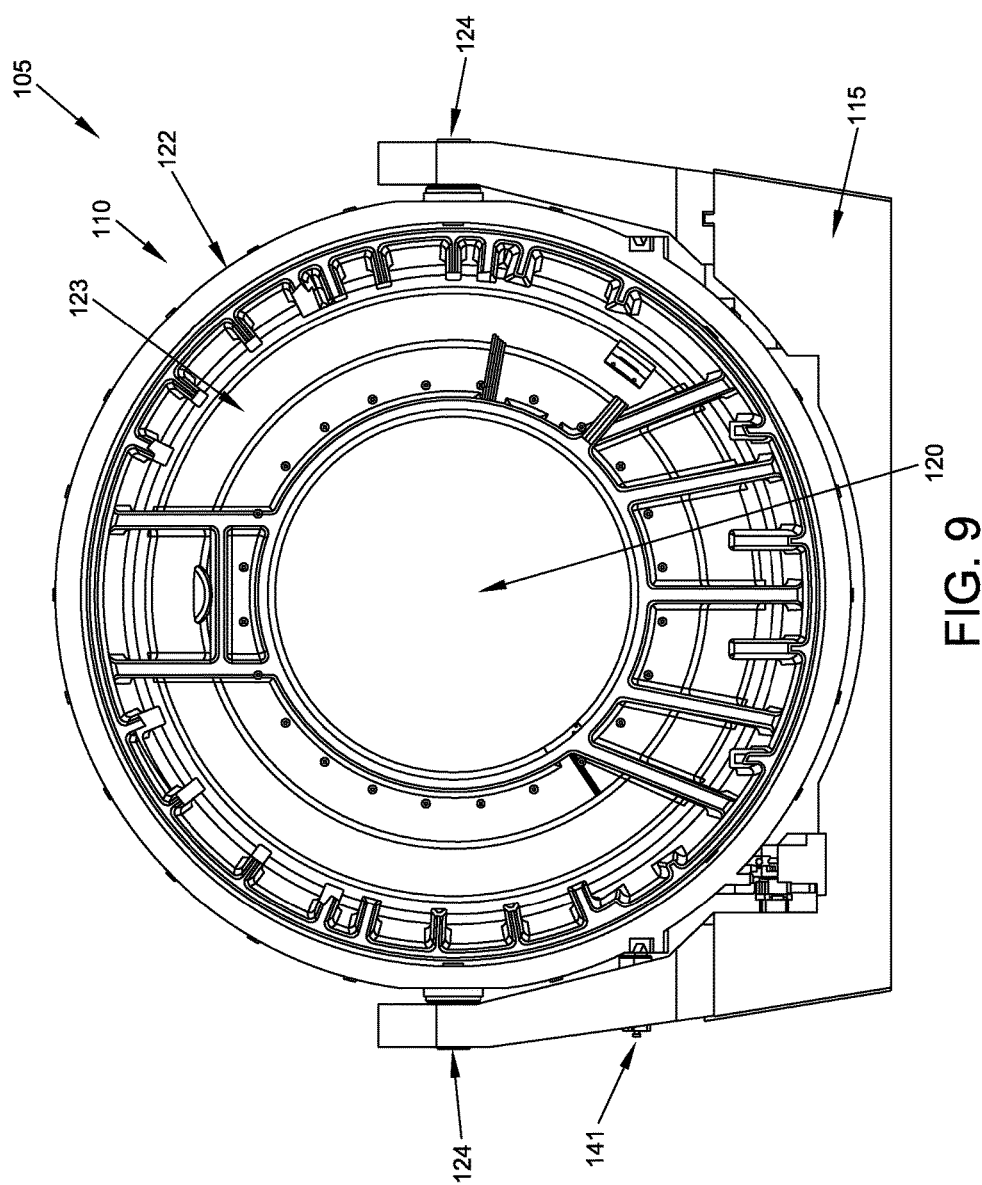
Figure 10:
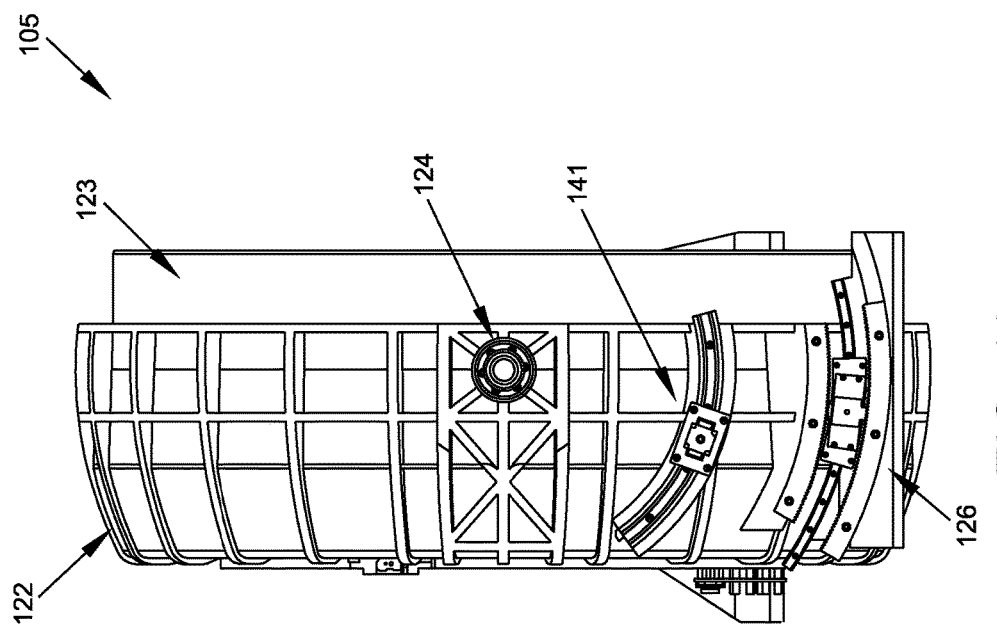
Figure 11:
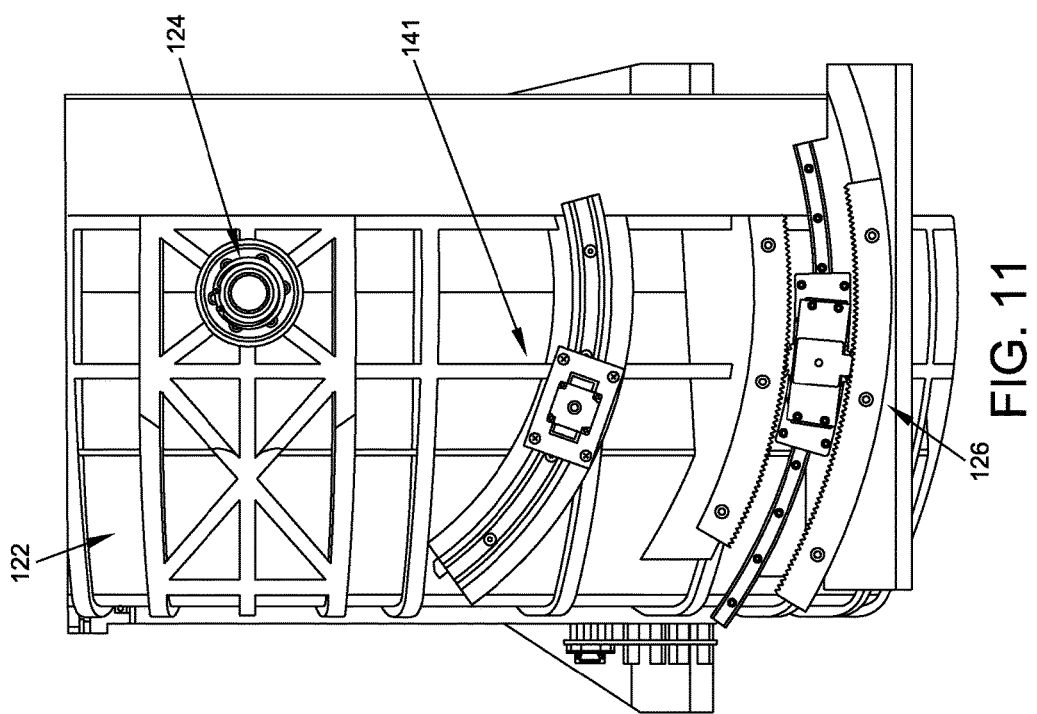
Figure 12:
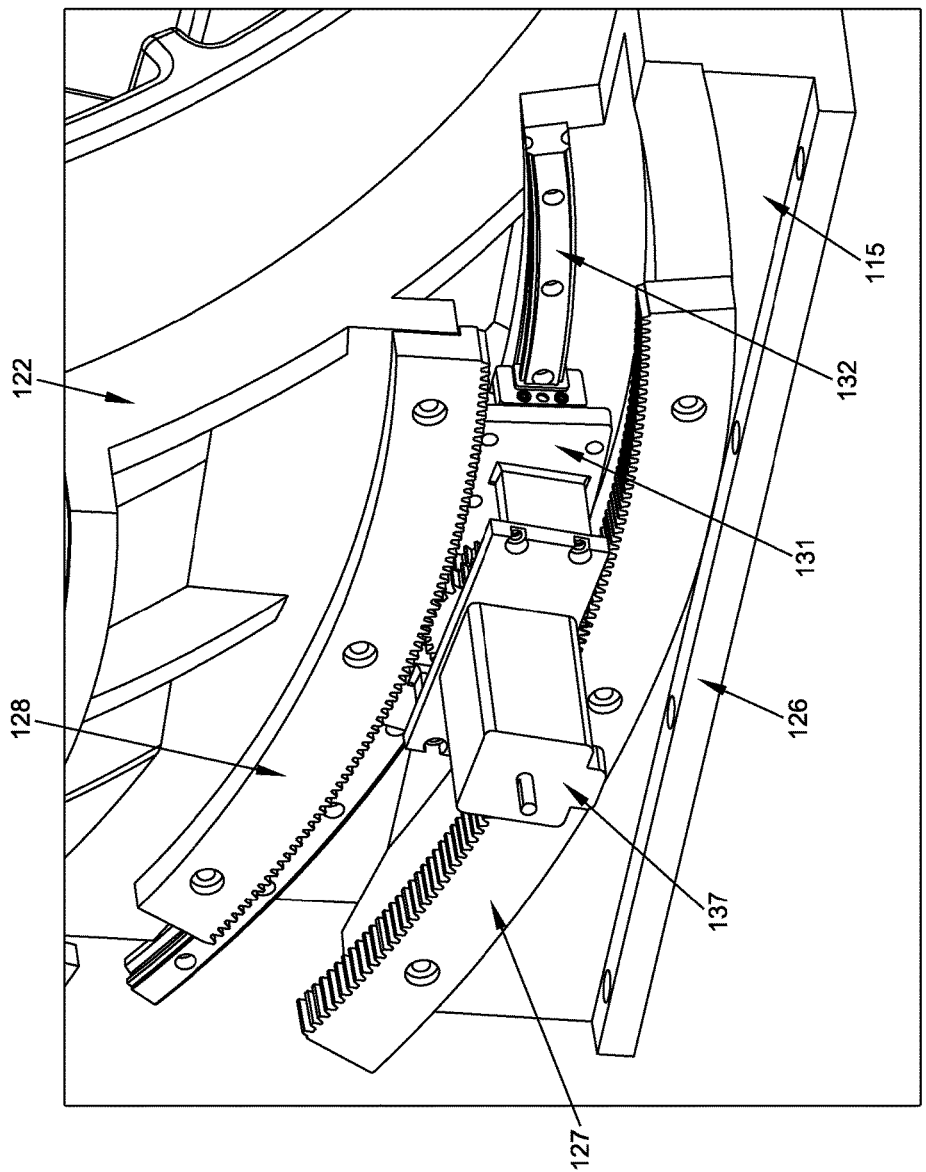
Figure 13:
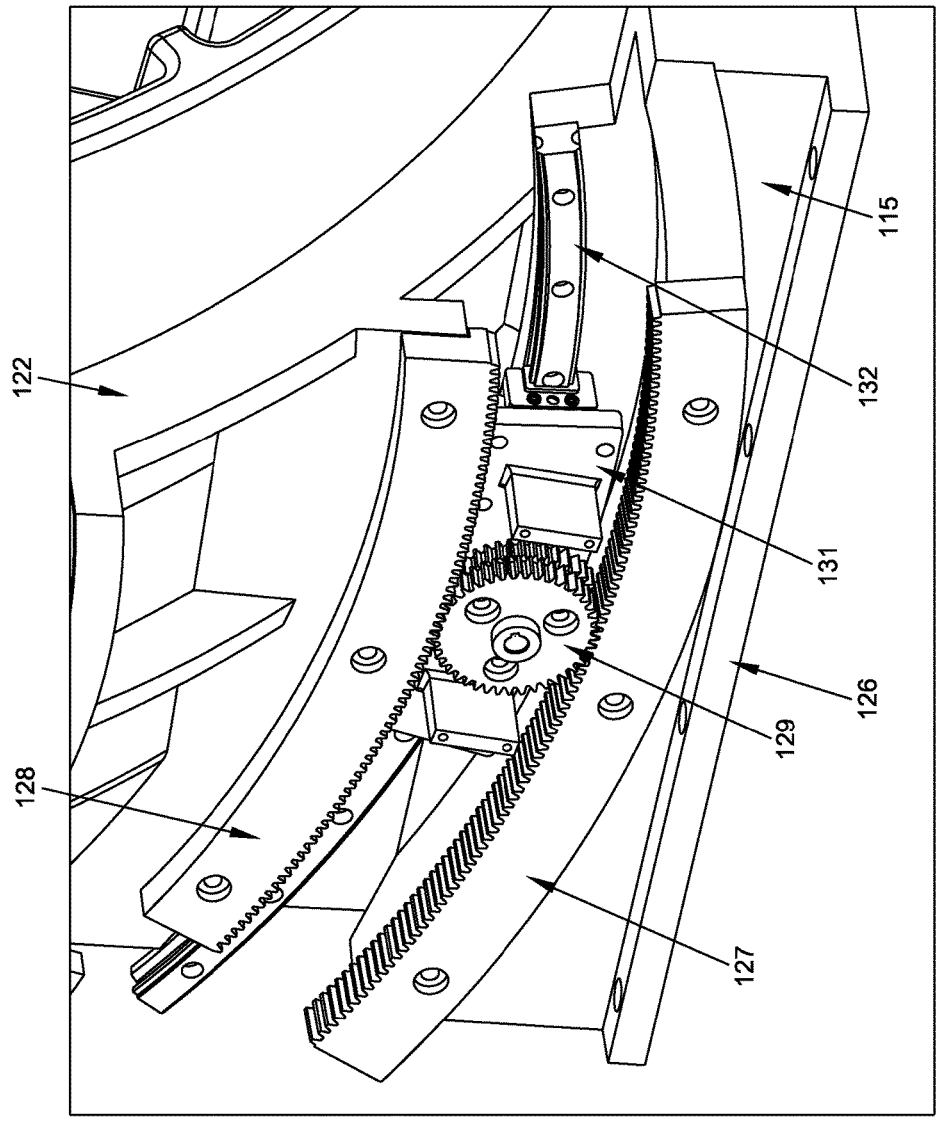
Figure 14:
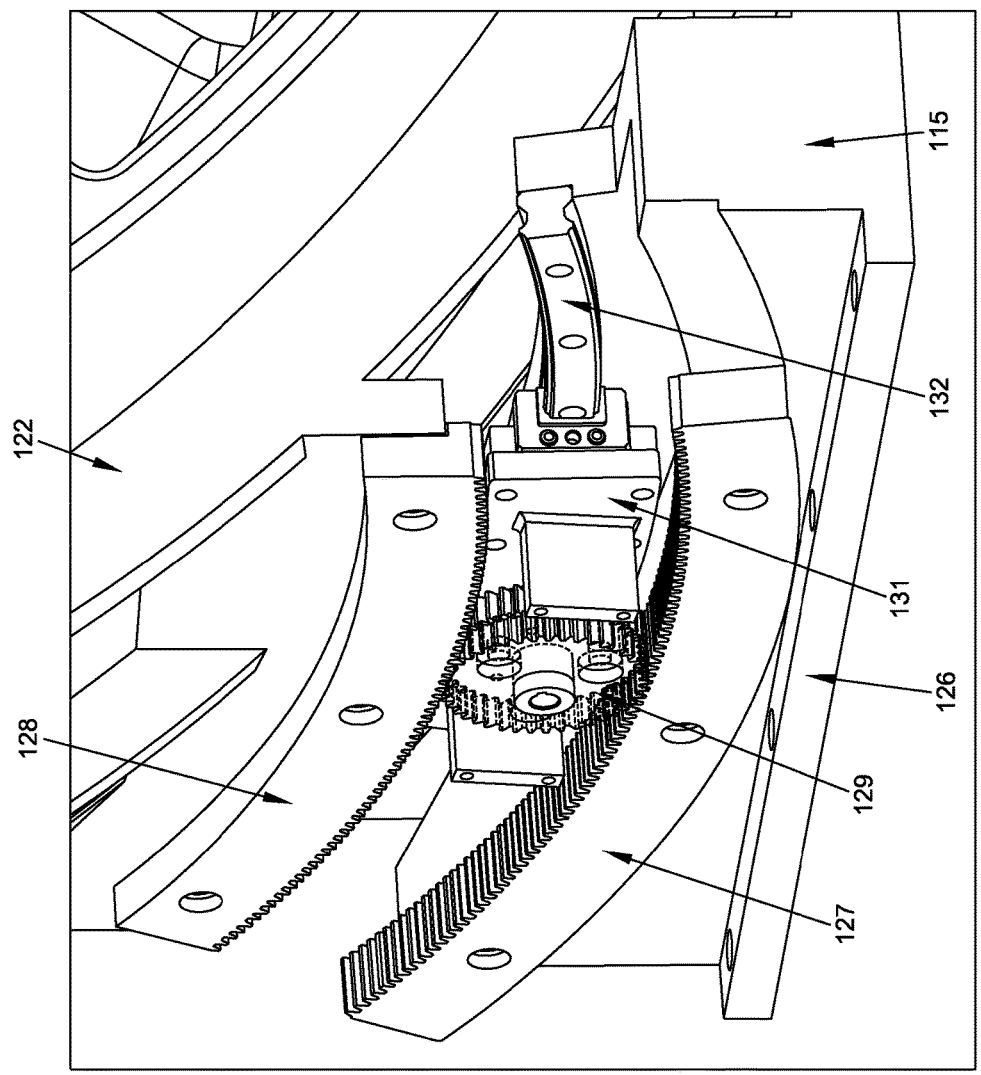

Anatomical Imaging System with Tilting Torus, Tilt Brake and Fail-Safe Brake

In accordance with the present invention, there is provided a novel apparatus for selectively tilting the torus 110 of a CT imaging system 105 which minimizes the profile of the CT imaging system 105 while also maximizing the degree to which the torus 110 of the CT imaging system 105 may be tilted.

The present invention also comprises the provision and use of novel apparatus for maintaining the tilt angle of the torus 110 of a CT imaging system 105 at a desired angle relative to the base 115 of the CT imaging system 105 after the torus 110 has been tilted.

The present invention further comprises the provision and use of novel fail-safe brake 151 for preventing the torus 110 of the CT imaging system 105 from moving (i.e., tilting) relative to the base 115 of the CT imaging system 105 in the event that power to the CT imaging system 105 is interrupted.

Looking now at FIGS. 8-17, there is shown a novel CT imaging system 105 which generally comprises a torus 110 which is supported by a base 115. A center opening 120 is formed in torus 110. Center opening 120 receives the patient anatomy which is to be scanned.

Torus 110 generally comprises a gantry 122 and a rotating disc 123. Gantry 122 is secured to base 115 by a pair of pivoting connectors 124 located on either side of gantry 122, such that gantry 122 (and hence torus 110) can pivot on pivoting connectors 124 relative to base 115, whereby to tilt torus 110 relative to base 115. Rotating disc 123 is rotatably disposed within gantry 122, such that rotating disc 123 can rotate circumferentially around center opening 120 without moving gantry 122. Rotating disc 123 generally comprises scanning components (e.g., the aforementioned X-ray tube assembly 25 and X-ray detector assembly 30, etc.) which are mounted to rotating disc 123 circumferentially around center opening 120, whereby to permit scanning of an object (e.g., a patient) disposed within center opening 120 (for the sake of clarity, the scanning apparatus is omitted from FIGS. 8-17).

As seen in FIGS. 8-17, CT imaging system 105 comprises a novel planetary gear 126 which may be used to selectively tilt torus 110 relative to base 115. More particularly, planetary gear 126 generally comprises a curved lower planet gear 127 which is mounted to base 115, a curved upper planet gear 128 which is mounted to gantry 122, and a sun gear 129 which is rotatably disposed between lower planet gear 127 and upper planet gear 128, such that the teeth of sun gear 129 are in constant contact with both lower planet gear 127 and upper planet gear 128, as will hereinafter be discussed in greater detail. Sun gear 129 is mounted to a carrier 131 which is in turn slidably mounted to a slide 132 which is mounted to base 115, such that carrier 131 (and sun gear 129 mounted to carrier 131) can move along slide 132 (and hence along base 115). A motor 137 (FIG. 12) may be used to selectively rotate sun gear 129 (either clockwise or counterclockwise), as desired.

By virtue of the foregoing construction, rotation of sun gear 129 by motor 137 causes sun gear 129 to "walk" along lower planet gear 127 as the teeth of sun gear 129 interface with the teeth of lower planet gear 127. As sun gear 129 "walks" along lower planet gear 127, carrier 131 moves along slide 132 (i.e., in the same direction that sun gear 129 "walks" along lower planet gear 127). At the same time, the rotation of sun gear 129 causes upper planet gear 128 to move relative to sun gear 129 (i.e., in the opposite direction that sun gear 129 is "walking" relative to lower planet gear 127). Hence, the effect of rotating sun gear 129 is effectively doubled (i.e., because sun gear 129 moves along lower planet gear 127 at the same time that upper planet gear 128 is moving along the moving sun gear 129).

Figure 15:
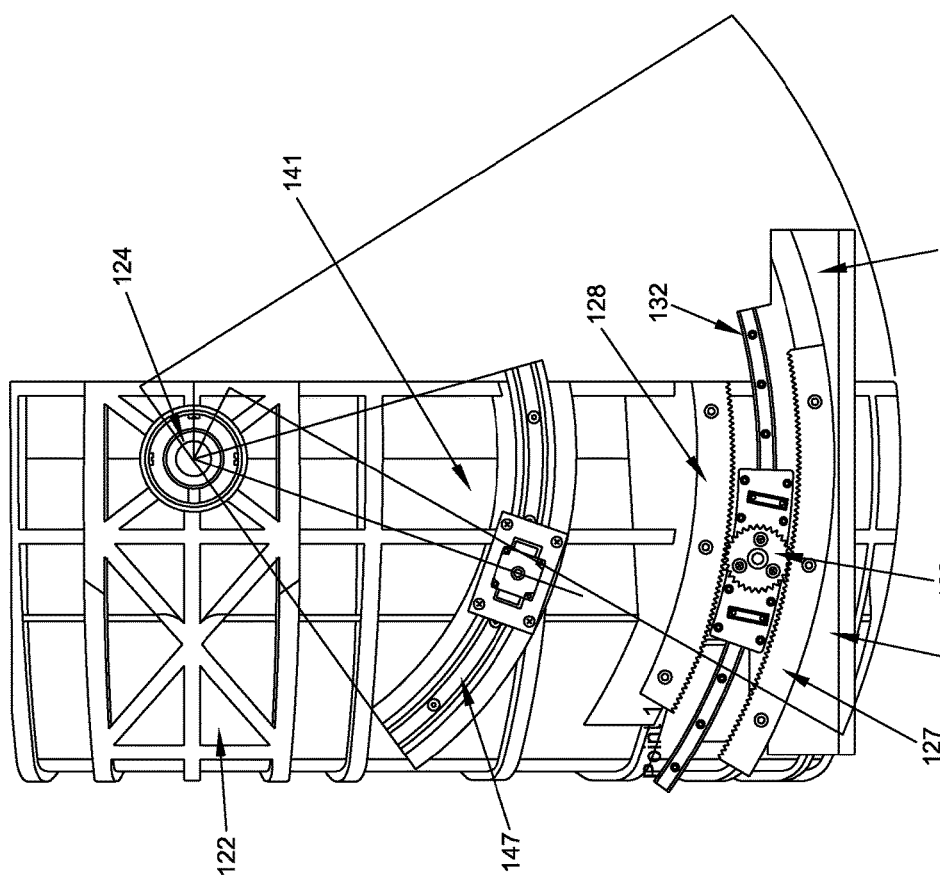
Figure 16:
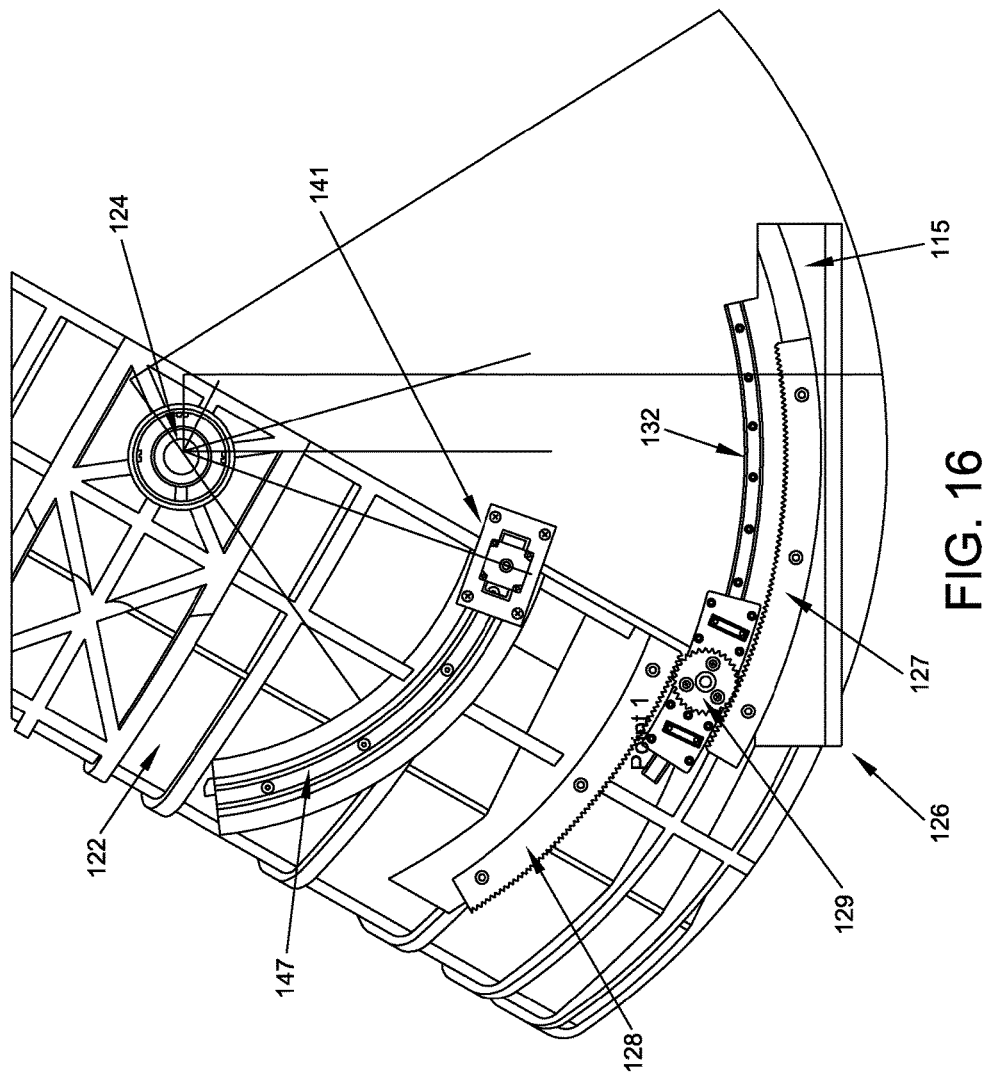

By way of example but not limitation, and looking now at FIG. 15, it will be appreciated that when sun gear 129 is centered relative to both lower planet gear 127 and upper planet gear 128, torus 110 is disposed perpendicular to base 115 (i.e., torus 110 is not tilted). As sun gear 129 is rotated counterclockwise (from the angle of view of FIG. 15), sun gear 129 walks clockwise along lower planet gear 127 while upper planet gear 128 moves counterclockwise on sun gear 129, whereby to tilt torus 110 in a first clockwise direction relative to base 115 (see FIG. 16).

Figure 17:
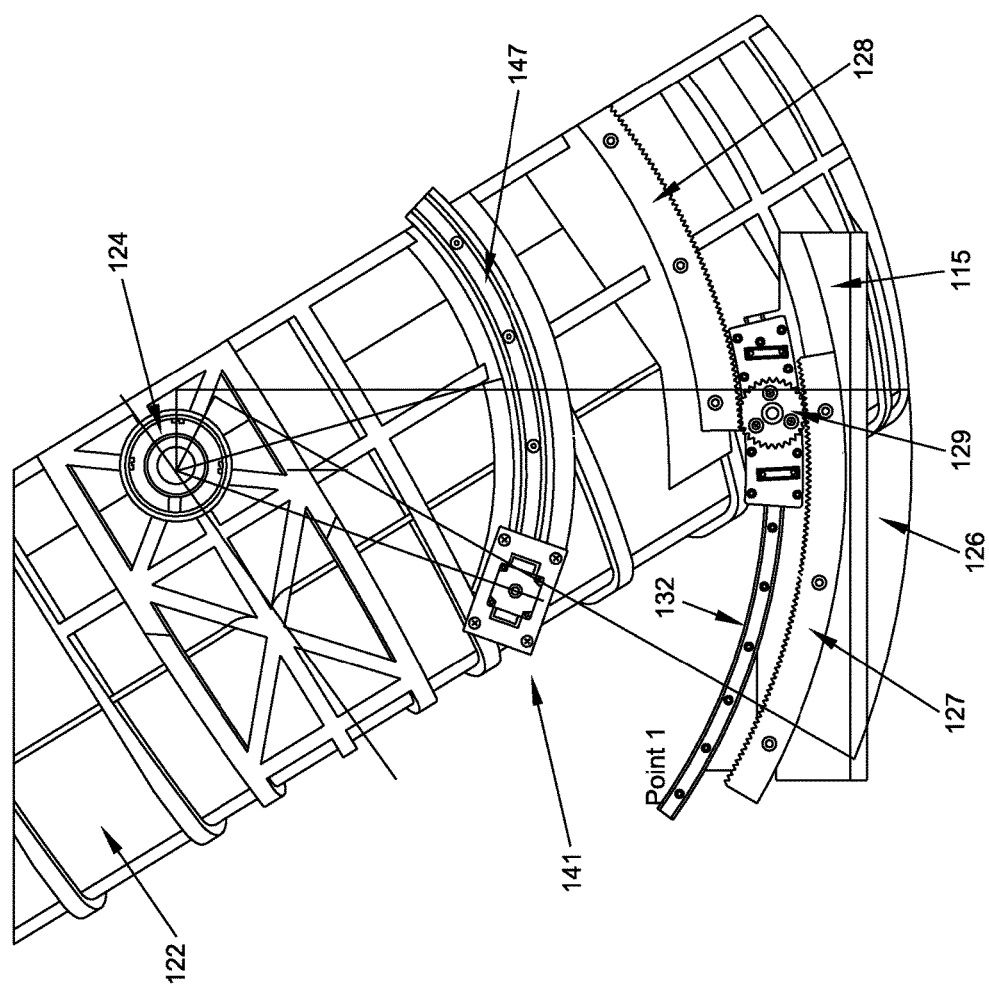
Figure 18:
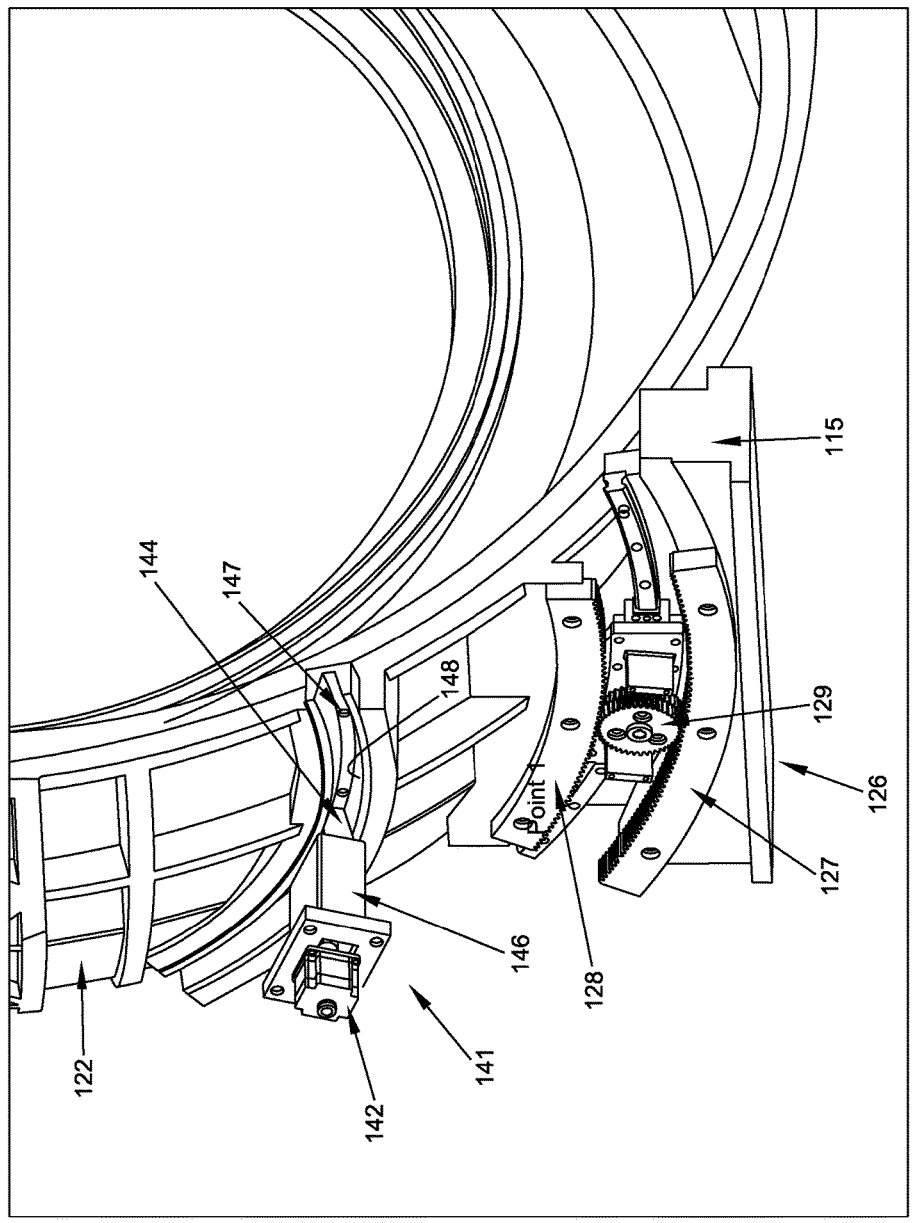
FIGS. 18-22 are schematic views showing a novel brake for selectively preventing the torus of a CT imaging system from moving.
Figure 19:
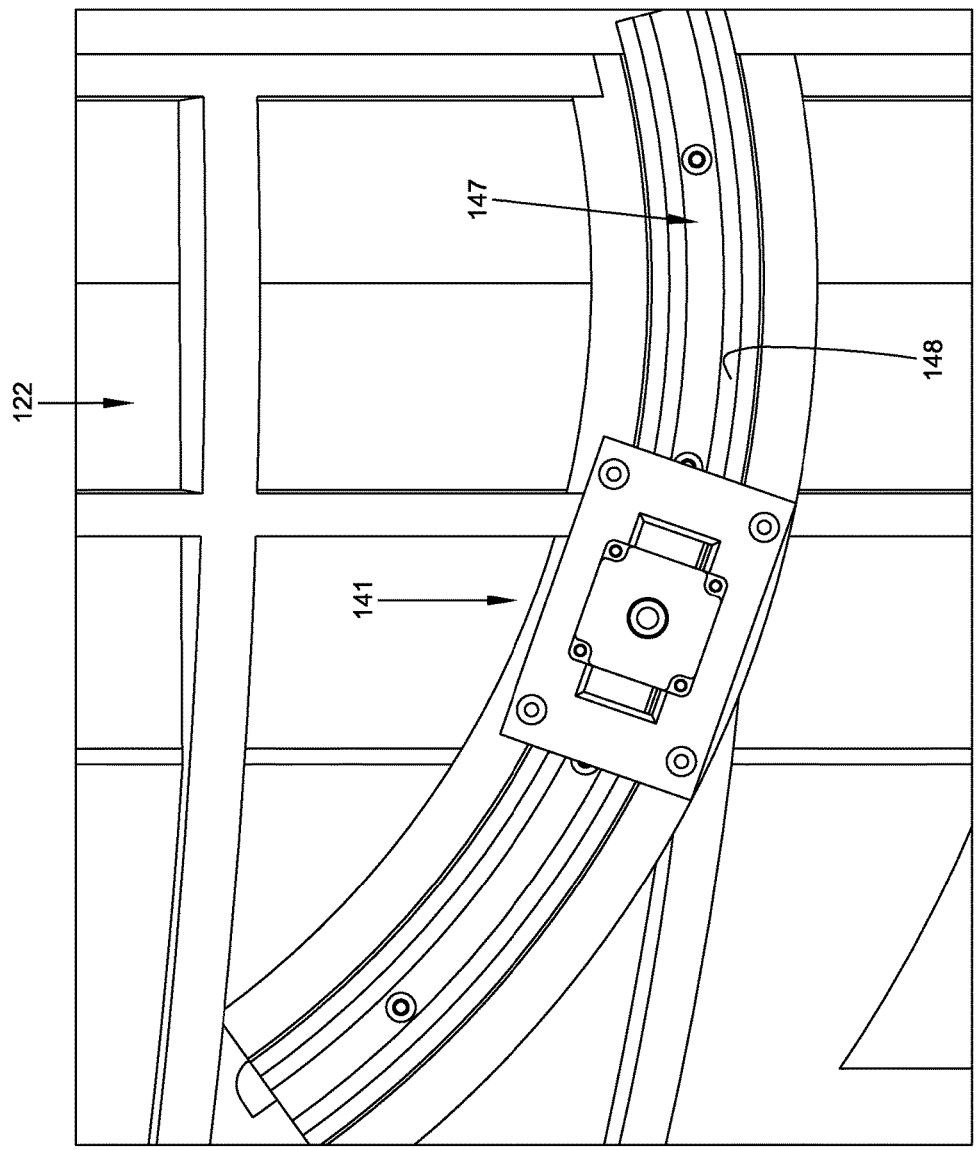
Figure 20:
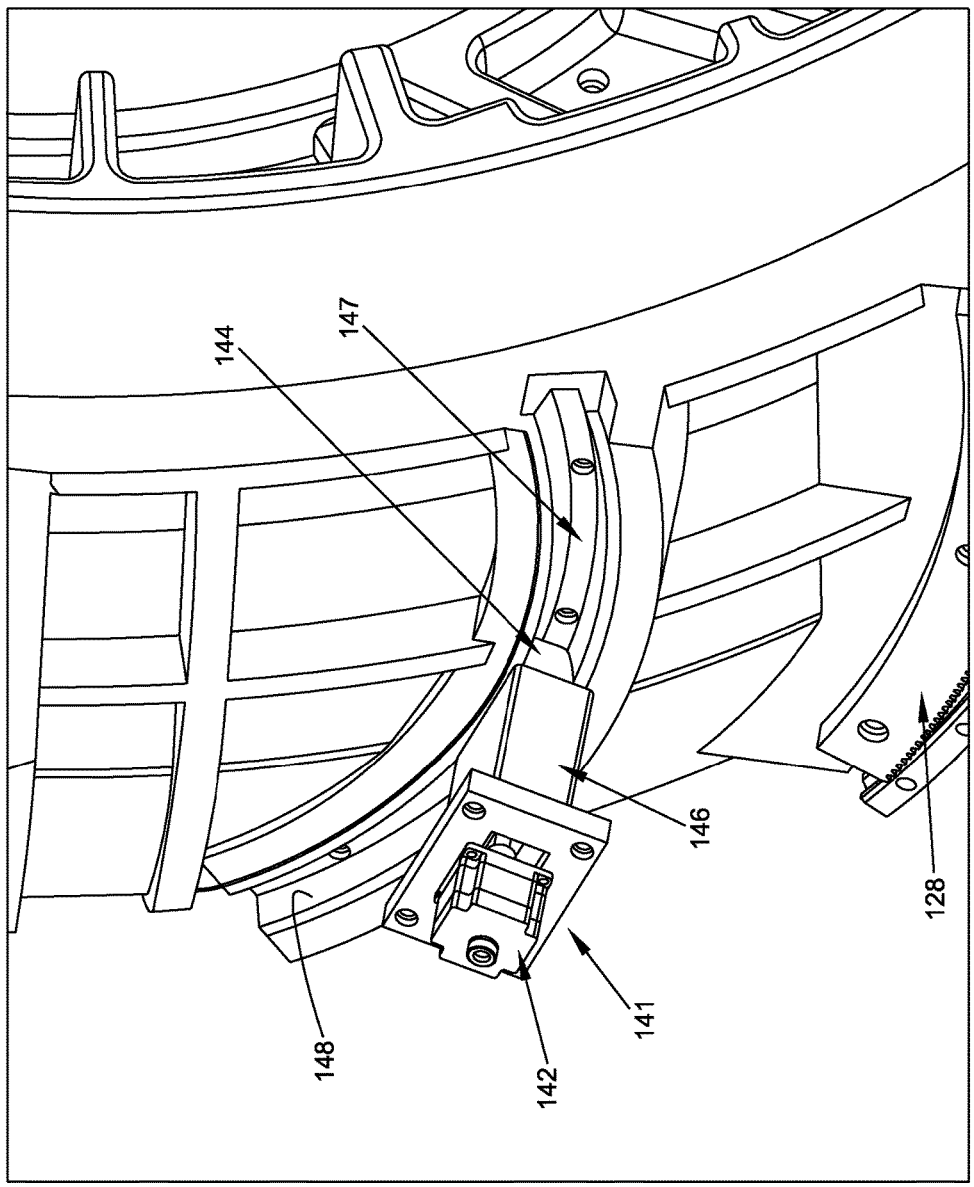
Figure 21:
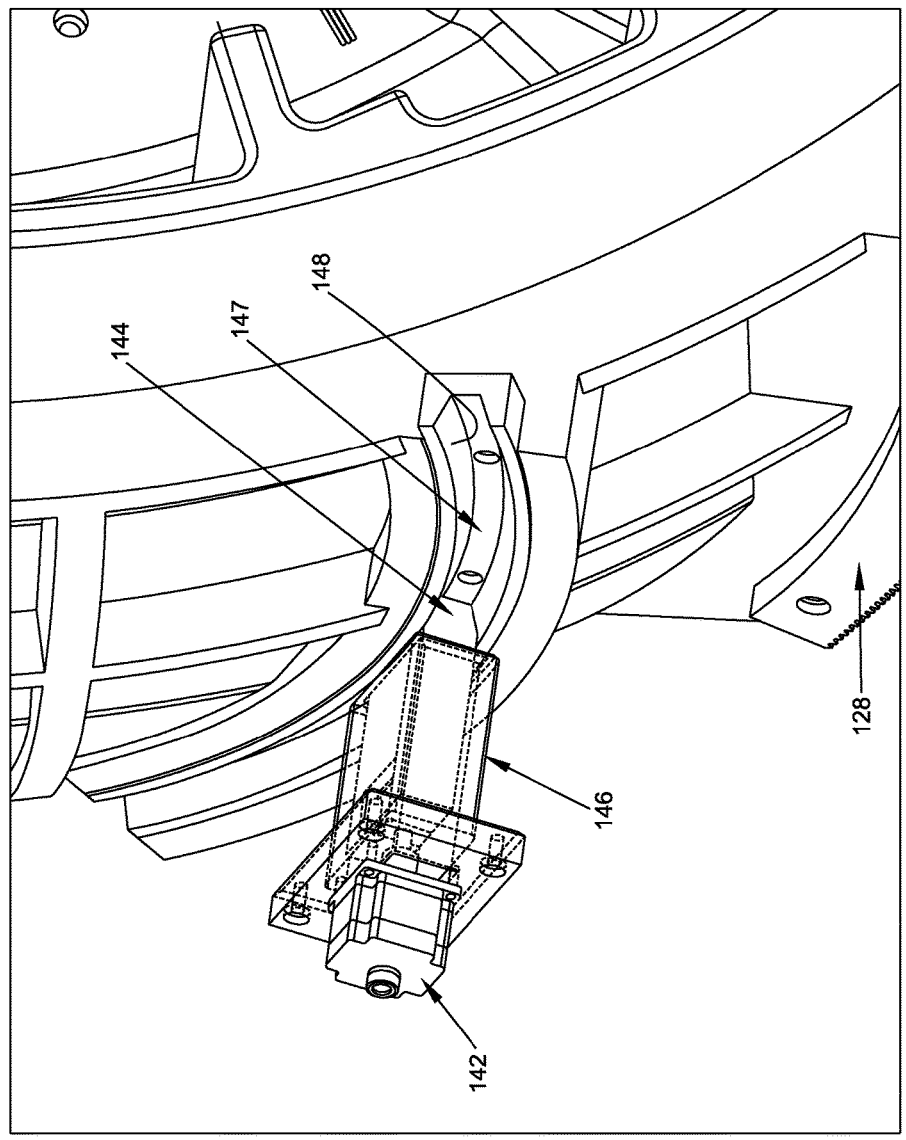
Figure 22:
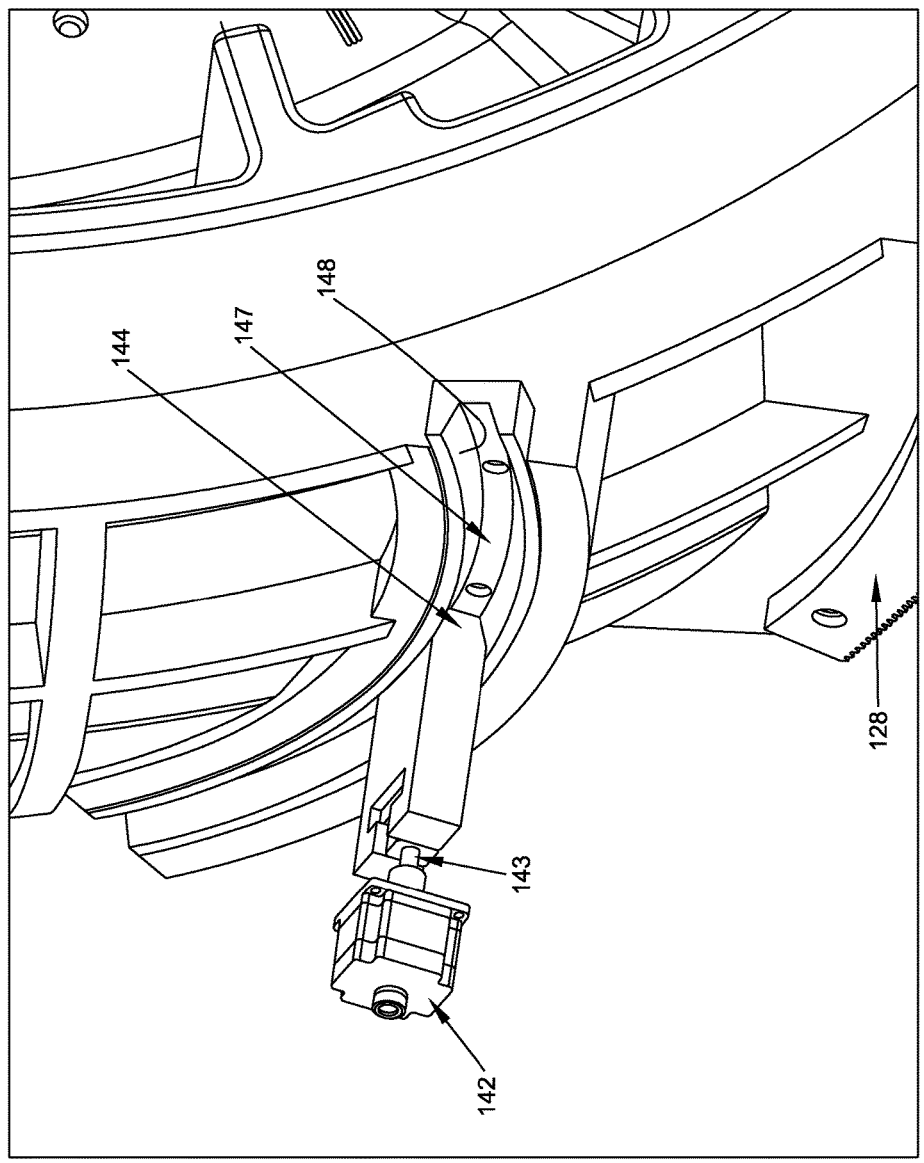

Looking next at FIG. 17, it will be seen that when sun gear 129 is rotated in a clockwise direction (as seen from the angle of view of FIG. 17), sun gear 129 walks in the opposite direction (i.e., counterclockwise) along lower planet gear 127, and upper planet gear 128 is moved counterclockwise on sun gear 129. Hence, by virtue of rotating sun gear 125 in a clockwise direction, torus 110 is tilted in a second, counterclockwise direction relative to base 115.

Therefore, by selectively rotating sun gear 155 either clockwise or counterclockwise, and by controlling how far sun gear 129 walks along lower planet gear 127, torus 110 may be tilted in the direction and to the degree (relative to base 115) which is desired.

It will be appreciated that the degree to which torus 110 is permitted to tilt relative to base 115 is a function of the degree of curvature of lower planet gear 127 and upper planet gear 128, as well as a function of the length of lower planet gear 127 and upper planet gear 128. It will also be appreciated that, by virtue of the foregoing construction, permanent arc-shaped tilt guides which enlarge the profile of CT imaging system 105 are no longer necessary, inasmuch as lower planet gear 127 and upper planet gear 128 effectively combine to form a tilt guide that is the combined length of lower planet gear 127 and upper planet gear 128, and which extend outboard of base 115 only when tilting is required and torus 110 is being actively tilted. This is a significant improvement in the art.

It will be appreciated that it may be desirable to provide a brake for maintaining the tilt of torus 110 while CT imaging system 105 is used for scanning. To this end, and looking next at FIGS. 18-22, there is shown a brake 141. Brake 141 generally comprises an actuator 142 having an actuating shaft 143, and a wedge 144 secured to the free end of actuating shaft 143. Actuator 142 is secured to a housing 146 which is securely mounted to base 115. Housing 146 is disposed over actuating shaft 143 and a portion of wedge 144 so that wedge 144 selectively projects out of housing 146. Wedge 144 is sized to make an interference fit with an arcuate groove 147 that is formed in gantry 122 when wedge 144 is moved toward gantry 122 by actuator 143. Arcuate groove 147 comprises inclined side walls 148 which are contacted by wedge 144 such that when wedge 144 is driven into arcuate groove 147 by actuator 142, arcuate groove 147

(and hence torus 110) cannot pivot relative to actuator 143 (and hence relative to base 115).

In use, when it is desired to pivot (i.e., tilt) torus 110 relative to base 115, actuator 142 is actuated so as to retract its actuating shaft 143 outwardly, away from torus 110, and hence to withdraw wedge 144 out of arcuate groove 147. Planetary gear 126 is then utilized to tilt torus 110 as desired relative to base 115 in the manner discussed above. When torus 110 has been tilted to the desired angle, actuator 142 is actuated so as to move actuating shaft 144 toward torus 110, and hence to drive wedge 144 into arcuate groove 147 and thereby establish a secure interference fit between wedge 144 and groove 147. When wedge 144 makes a secure interference fit with arcuate groove 147, torus 110 is effectively "locked" at the angle at which it has been tilted.

It has also been recognized that, in the event of a power failure, brake 141 could fail (e.g., actuator 142 may fail to force wedge 144 securely into arcuate groove 147, thereby allowing torus 110 to "fall" or "swing" away from a given tilted position on pivoting connectors 124. Because torus 110 is typically quite large, and because unexpected and uncontrolled falling/swinging of torus 110 may present a hazard to personnel operating CT imaging system 105 and/or to patients undergoing scanning by CT imaging system 105, it can be desirable to provide a fail-safe brake for maintaining torus 110 in a tilted configuration in the event of such a power failure.

Figure 23:
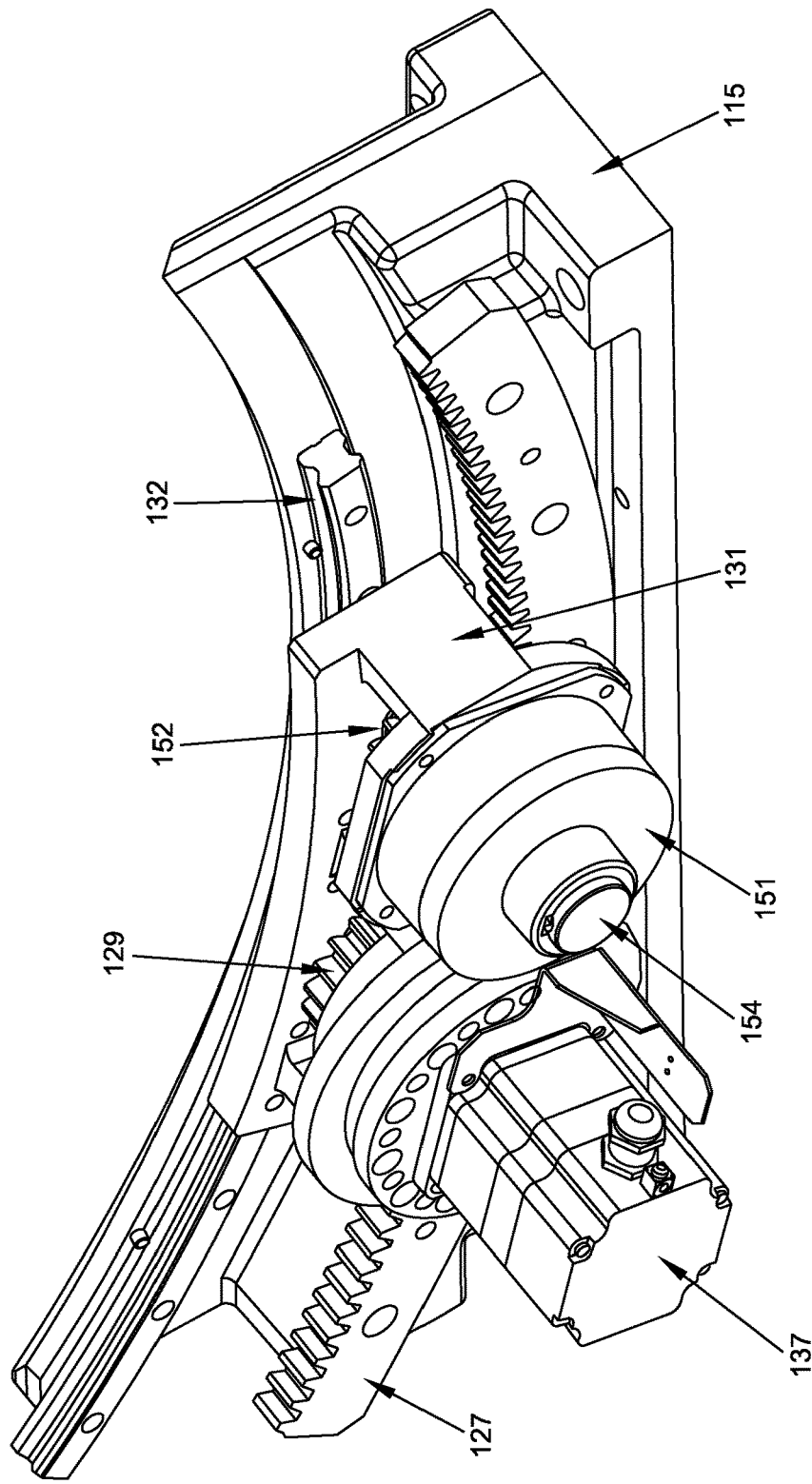
FIGS. 23 and 24 are schematic views showing a novel fail-safe brake for preventing the torus of a CT imaging system from moving in the event of a power interruption.
Figure 24:
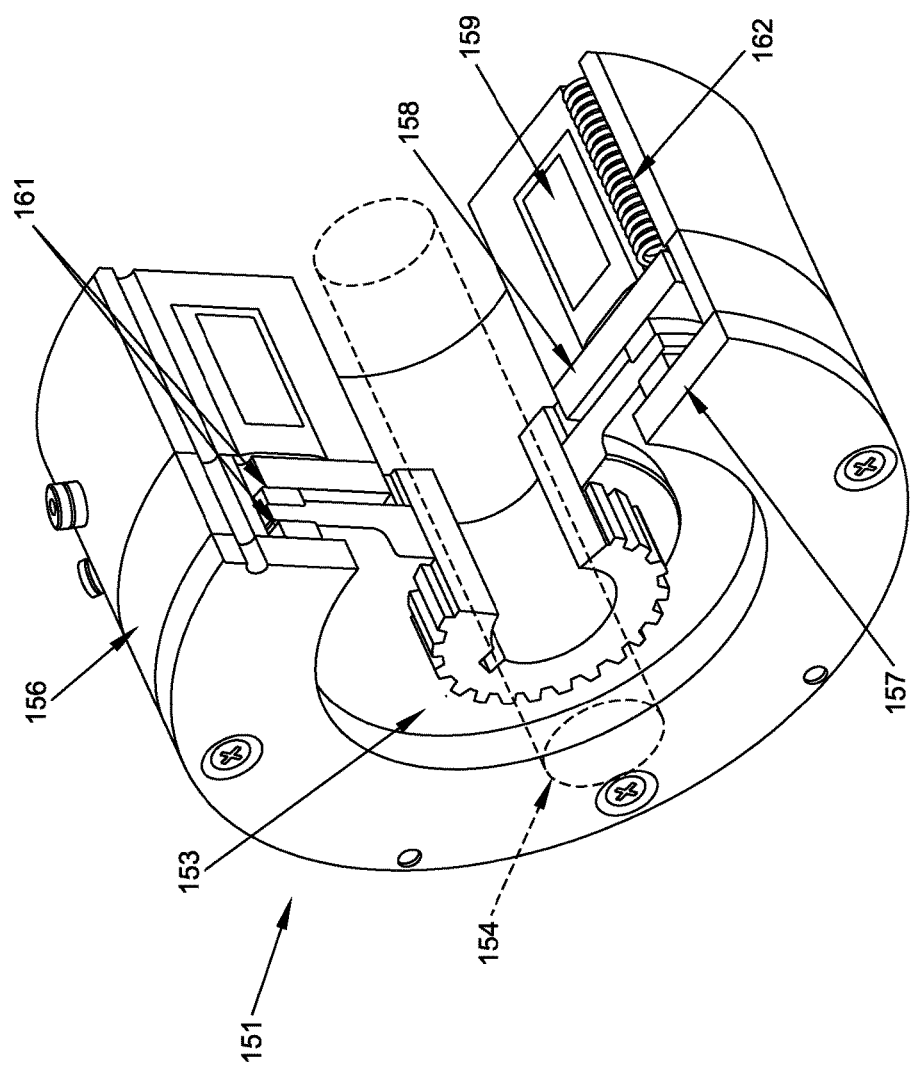

To that end, and looking now at FIGS. 23 and 24, a fail-safe brake 151 may be provided. Fail-safe brake 151 generally comprises a gear 152 and a disc 153, with a shaft 154 being disposed between gear 152 and disc 153. A housing 156 covers at least some of fail-safe brake 151, as will hereinafter be discussed in greater detail. Gear 152 and disc 153 are connected to shaft 154 such that when gear 152 rotates, disc 153 also rotates, and vice versa. Housing 156 comprises an end plate 157, an armature 158 and a coil 159. Disc 153 is disposed within housing 156 in a gap between end plate 157 and armature 158. High-friction pads 161 (e.g., asbestos pads) are disposed on the sides of end plate 157 and armature 158 which face disc 153. A spring 162 biases armature 158 toward disc 153 such that high-friction pad 161 contacts disc 153 under the power of spring 162 and pushes disc 153 toward the high-friction pad 161 carried by end plate 157, whereby to cause disc 153 to be clamped therebetween and prevent rotation of gear 152. When electric current is passed through coil 159, coil 159 generates an electromagnetic field which pulls armature 158 toward coil 159 (and against the power of spring 162). When armature 158 is drawn toward coil 159, disc 153 is free to rotate (and hence, shaft 154 and gear 152 are also free to rotate). By virtue of the foregoing construction, it will be appreciated that, if CT imaging system 105 should suffer a power failure, the electromagnetic field generated by coil 159 will fail, thereby causing spring 162 to bias armature 158 toward disc 153 such that high-friction pads 161 engage disc 153, clamping disc 153 between end plate 157 and armature 158. This action prevents rotation of disc 153 (and hence also prevents rotation of gear 152).

In one preferred form of the present invention, fail-safe brake 151 is carried on the aforementioned carrier 131 such that gear 152 contacts lower planet gear 127 (FIG. 23). Hence, when power is supplied to fail-safe brake 151 so that gear 152 is free to rotate, gear 152 will rotate when sun gear 129 rotates (i.e., when the tilt angle of torus 110 is changed). Conversely, when a power failure causes disc 153 to be clamped by fail-safe break 151 in the manner discussed above, gear 152 is unable to rotate, so that carrier 131 is unable to move and hence sun gear 129 is unable to move, whereby to lock the tilt angle of torus 110 until such time as electrical power is restored to CT imaging system 105. Thus, fail-safe brake 151 maintains the tilt angle of torus 110 in the event of a power failure.

Anatomical Imaging System with Fixed Cup-Shaped Gantry and Rotating Cup-Shaped Disc In accordance with the present invention, there is provided a novel CT imaging system comprising a fixed cup-shaped gantry and a rotating cup-shaped disc which is positioned within the fixed cup-shaped gantry, whereby to provide enhanced structural integrity so as to provide increased stability for the components that are mounted to the rotating cup-shaped disc when the rotating cup-shaped disc is rotated and hence to provide improved image quality. The present invention also comprises the provision and use of a new way for mounting components (e.g., X-ray tube assembly 25, X-ray detector assembly 30, etc.) to the rotating disc so as to mitigate the destabilizing effects of the centrifugal forces that are imposed on the components when the rotating disc is rotated, i.e., by mounting the components to the interior side wall of the rotating cup-shaped disc.

Figure 25:
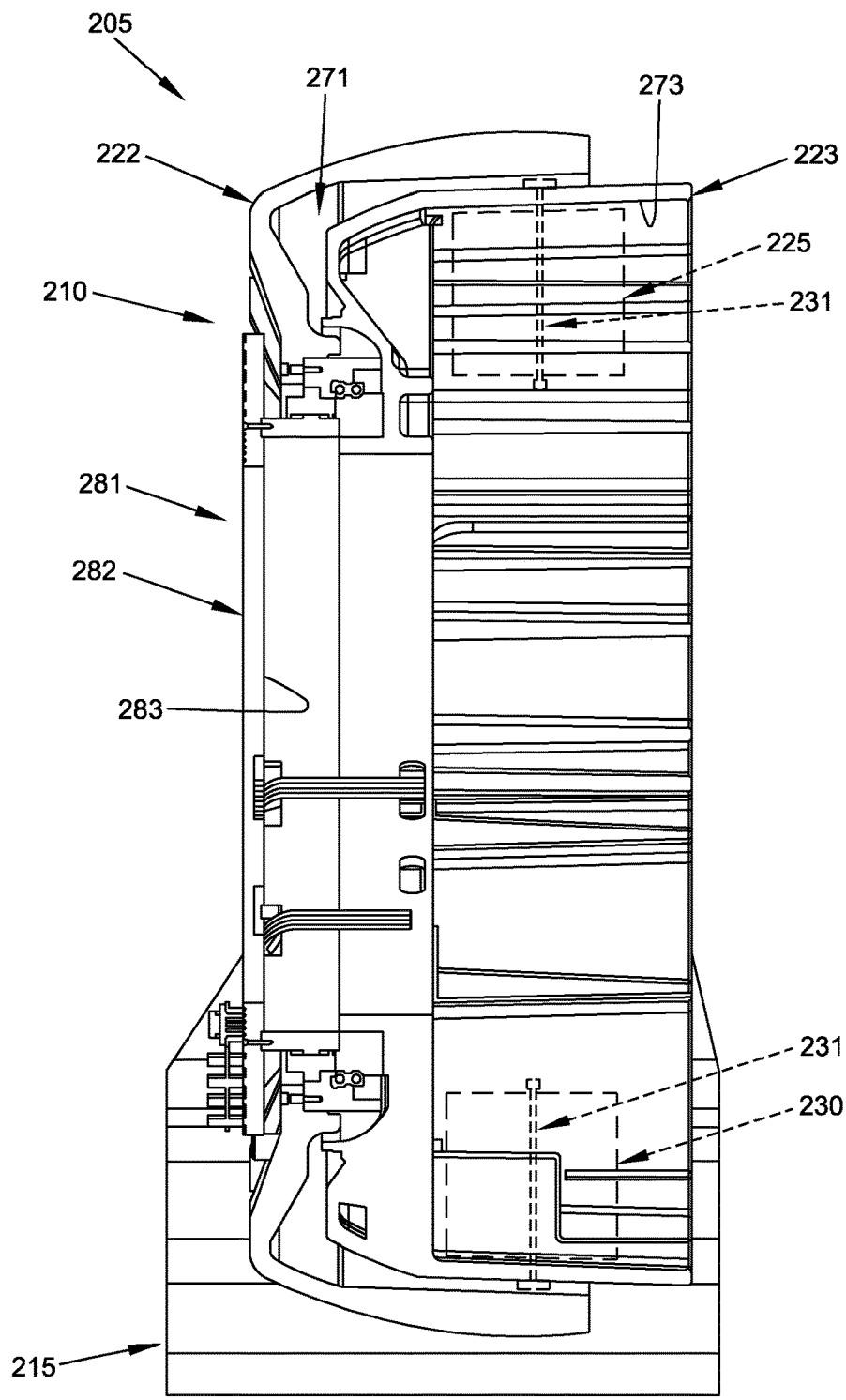
FIGS. 25-27 are schematic views showing a novel CT imaging system formed in accordance with the present invention, wherein the novel CT imaging system comprises a fixed cup-shaped gantry and a rotating cup-shaped disc, and further wherein the novel CT imaging system comprises a novel rotating slip ring.
Figure 26:
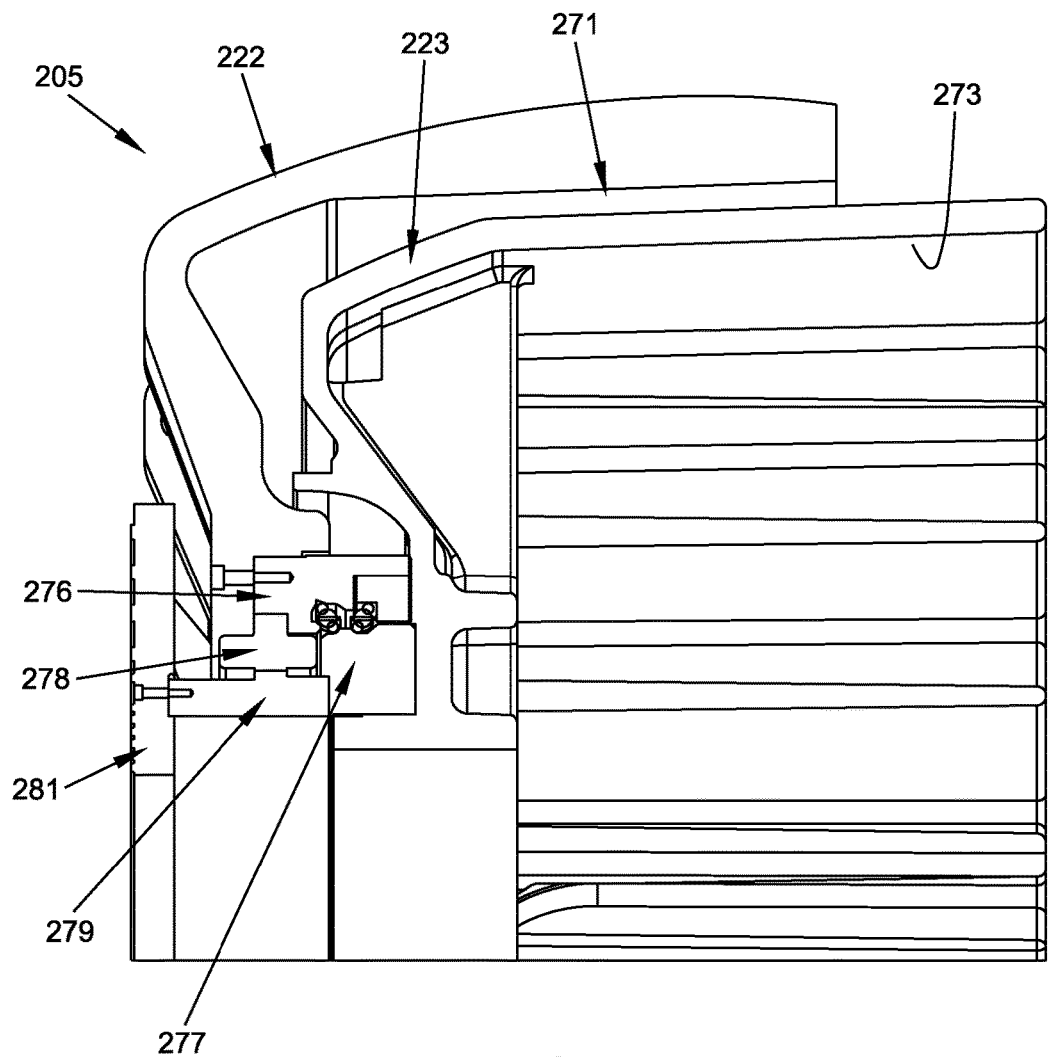
Figure 27:
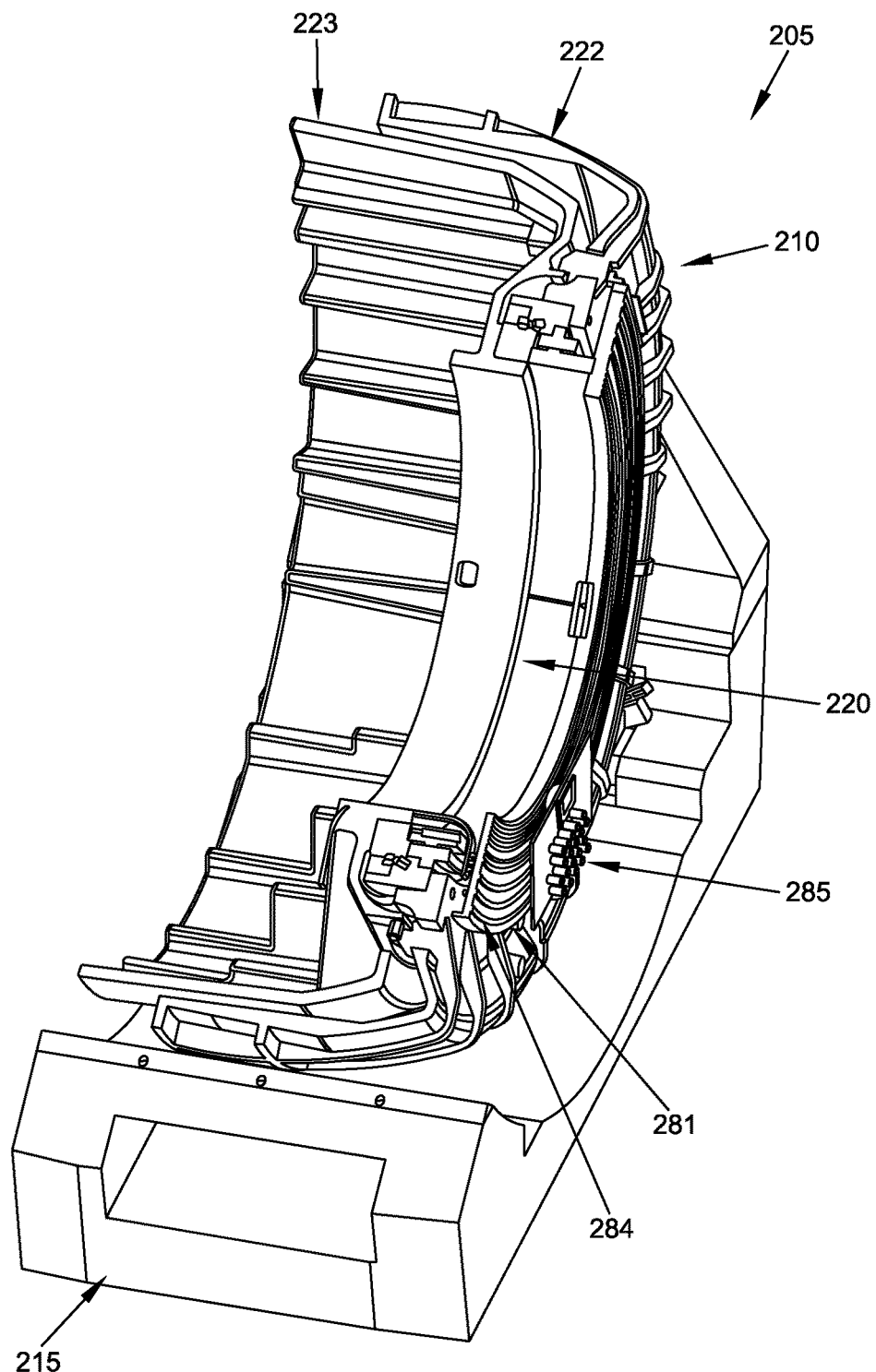
Figure 28:
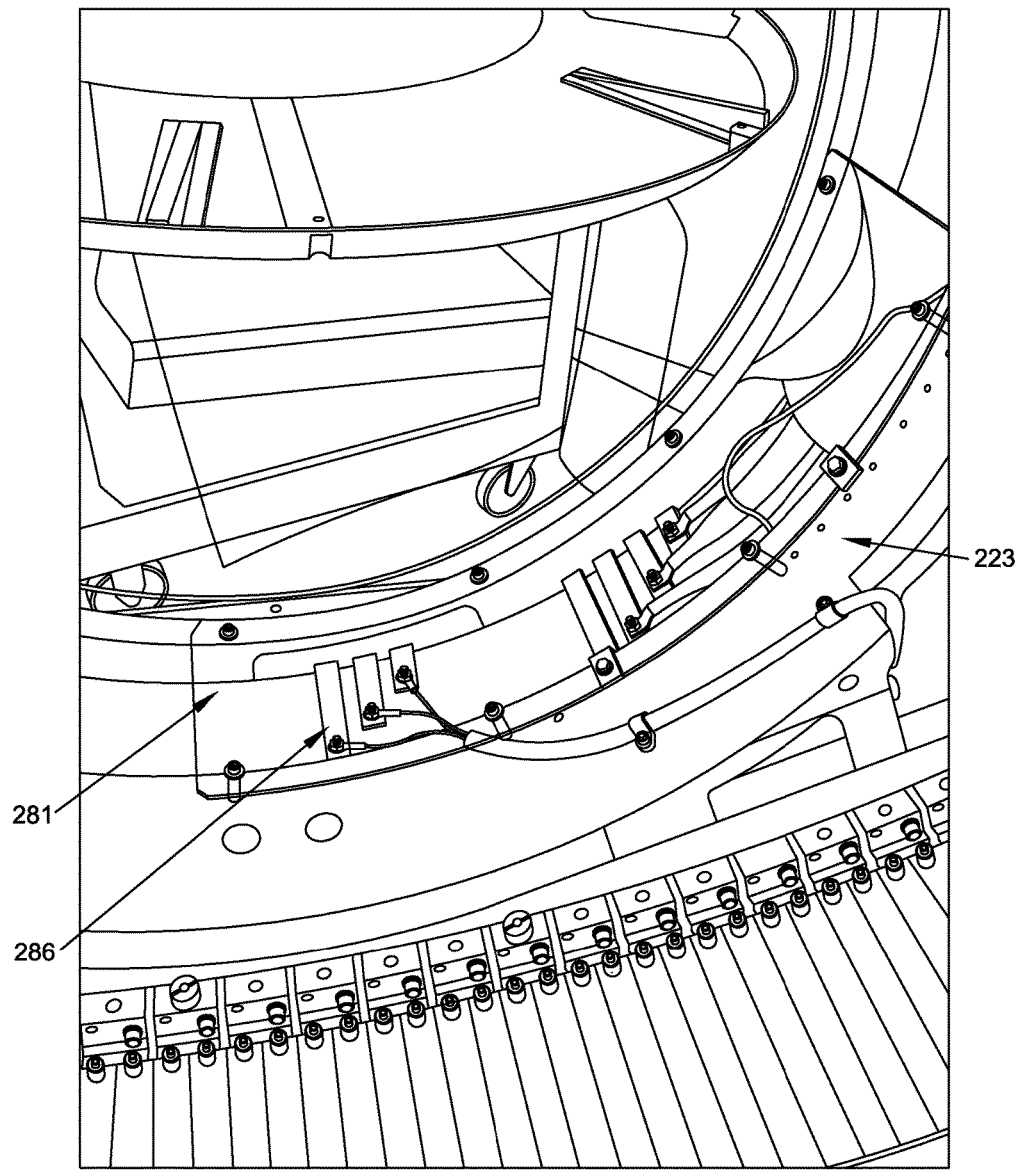
FIG. 28 is a schematic view showing further details of the novel slip ring shown in FIGS. 25-27.

Looking next at FIGS. 25-27, there is shown a novel CT imaging system 205 which generally comprises a torus 210 which is supported by a base 215. A center opening 220 (FIG. 27) is formed in torus 210. Center opening 220 receives the patient anatomy which is to be scanned.

Still looking at FIGS. 25-27, torus 210 generally comprises a fixed cup-shaped gantry 222 and a rotating cup-shaped disc 223. Fixed cup-shaped gantry 222 and rotating cup-shaped disc 223 are disposed concentrically about center opening 220.

Fixed cup-shaped gantry 222 comprises an inner cavity 271 for receiving rotating cup-shaped disc 223 therein. By forming the fixed gantry as a cup-shaped component, increased structural integrity is provided to fixed cup-shaped gantry 222.

Rotating cup-shaped disc 223 comprises an interior side wall 273 disposed concentrically about center opening 220. By forming the rotating disc as a cup-shaped component, increased structural integrity is provided to rotating cup-shaped disc 223. In one preferred form of the present invention, scanning components (e.g., the X-ray tube assembly 225 and X-ray detector assembly 230, etc., shown schematically in FIG. 25) are mounted to interior side wall 273 of rotating cup-shaped disc 223 with bolts 231 (also shown schematically in FIG. 25) which extend substantially radially, as shown in FIG. 25. It should be appreciated that, by mounting such scanning components to interior side wall 273 of rotating cup-shaped disc 223, centrifugal forces (i.e., forces that are generated when cup-shaped disc 223 is rotated) are directed radially outward toward interior side wall 273 of rotating cup-shaped disc 223, i.e., in the same direction that the scanning components (e.g., the X-ray tube assembly 225 and X-ray detector assembly 230, etc.) are bolted (e.g., with radially-extending bolts 231) to interior side wall 273 of rotating cup-shaped disc 223.

In other words, with the present invention, the scanning components (e.g., the X-ray tube assembly 225 and X-ray detector assembly 230, etc.) are bolted (e.g., with bolts 231) to interior side wall 273 of rotating cup-shaped disc 223 by passing the bolts 231 radially outward, substantially perpendicular to the adjacent portion of interior side wall 273. Thus, with the present invention, the centrifugal forces that are generated when cup-shaped disc 223 is rotated force the scanning components (e.g., the X-ray tube assembly 225 and X-ray detector assembly 230, etc.) radially outward against interior side wall 273 of rotating cup-shaped disc 223, with the scanning components being forced radially outward along the longitudinal axis of the bolts 231 securing the scanning components to interior side wall 273 of rotating cup-shaped disc 223.

As a result of this construction, the destabilizing effects of centrifugal forces on the scanning components that are mounted to interior side wall 273 of rotating cup-shaped disc 223 are mitigated, whereby to provide increased stability for the scanning components that are mounted to rotating cup-shaped disc 223.

In one preferred form of the invention, fixed cup-shaped gantry 222 comprises fixed gantry bearings 276, and rotating cup-shaped disc 223 comprises rotating disc bearings 277, whereby to facilitate rotation of rotating cup-shaped disc 223 within fixed cup-shaped gantry 222.

It should be appreciated that the increased structural integrity provided by forming the gantry as a cup-shaped gantry supplements the increased structural integrity provided by forming the rotating cup-shaped disc 223 as a cup-shaped disc, thereby further stabilizing rotating cup-shaped disc 223 when rotating cup-shaped disc 223 is rotated. Among other things, providing increased structural integrity for the fixed gantry and the rotating disc provides improved stability for the bearings mounted between the fixed gantry and the rotating disc, which results in increased image quality and extended bearing life.

In one preferred form of the present invention, CT imaging system 205 utilizes a direct drive motor for turning rotating cup-shaped disc 223 relative to fixed cup-shaped gantry 222. More particularly, in this form of the invention, fixed cup-shaped gantry 222 comprises a fixed coil 278 disposed circumferentially about center opening 220, and rotating cup-shaped disc 223 comprises a plurality of permanent magnets 279 disposed circumferentially about center opening 220, whereby to provide a direct drive motor for effecting rotation of rotating cup-shaped disc 223 relative to fixed cup-shaped gantry 222.

Rotating Slip Ring

The present invention further comprises the provision and use of a novel slip ring for providing electrical power to the rotating cup-shaped disc and/or to the components which are mounted to the rotating cup-shaped disc.

In order to provide electrical power to rotating cup-shaped disc 223 (whereby to power the scanning components mounted to rotating cup-shaped disc 223, e.g., X-ray tube assembly 225 and X-ray detector assembly 230, etc.), a novel rotating slip ring may also be provided for continuously transmitting electrical power to rotating cup-shaped disc 223 while rotating cup-shaped disc 223 is rotating.

More particularly, and looking now at FIGS. 25-30, a rotating slip ring 281 may be mounted to rotating cup-shaped disc 223. Rotating slip ring 281 preferably comprises an outer surface 282 and an inner surface 283. Outer surface 282 preferably comprises a plurality of concentric conductive strips 284 attached thereto for transmitting power and/or data from a connector 285 (FIG. 27) through rotating slip ring 281 to inner surface 283, and for transmitting data from inner surface 283 through slip ring 281 to connector 285. Connector 285 is preferably mounted to fixed cup-shaped gantry 222.

In one preferred form of the invention, electrical bus bars 286 (FIG. 28) are mounted to the inner surface 283 of rotating slip ring 281, whereby to provide electrical power and/or data to the components mounted to rotating cup-shaped disc 223 while rotating cup-shaped disc 223 is rotated, and/or to off-load data from the components mounted to rotating cup-shaped disc 223 while rotating cup-shaped disc 223 is rotated. Electrical bus bars 286 preferably extend perpendicular to the plane of slip ring 281 (and axially along opening 220), whereby to facilitate easy access to electrical bus bars 286 from the interior of CT imaging system 205. Preferably electrical bus bars 286 are secured to rotating slip ring 281 prior to mounting slip ring 281 within CT imaging system 205 so that slip ring 281 and electrical bus bars 286 may be manipulated as a unit during assembly and/or servicing of novel CT imaging system 205.

Position Sensor

And the present invention comprises the provision and use of a novel position sensor for determining the rotational disposition of the rotating cup-shaped disc relative to the fixed cup-shaped gantry in real-time.

Figure 29:
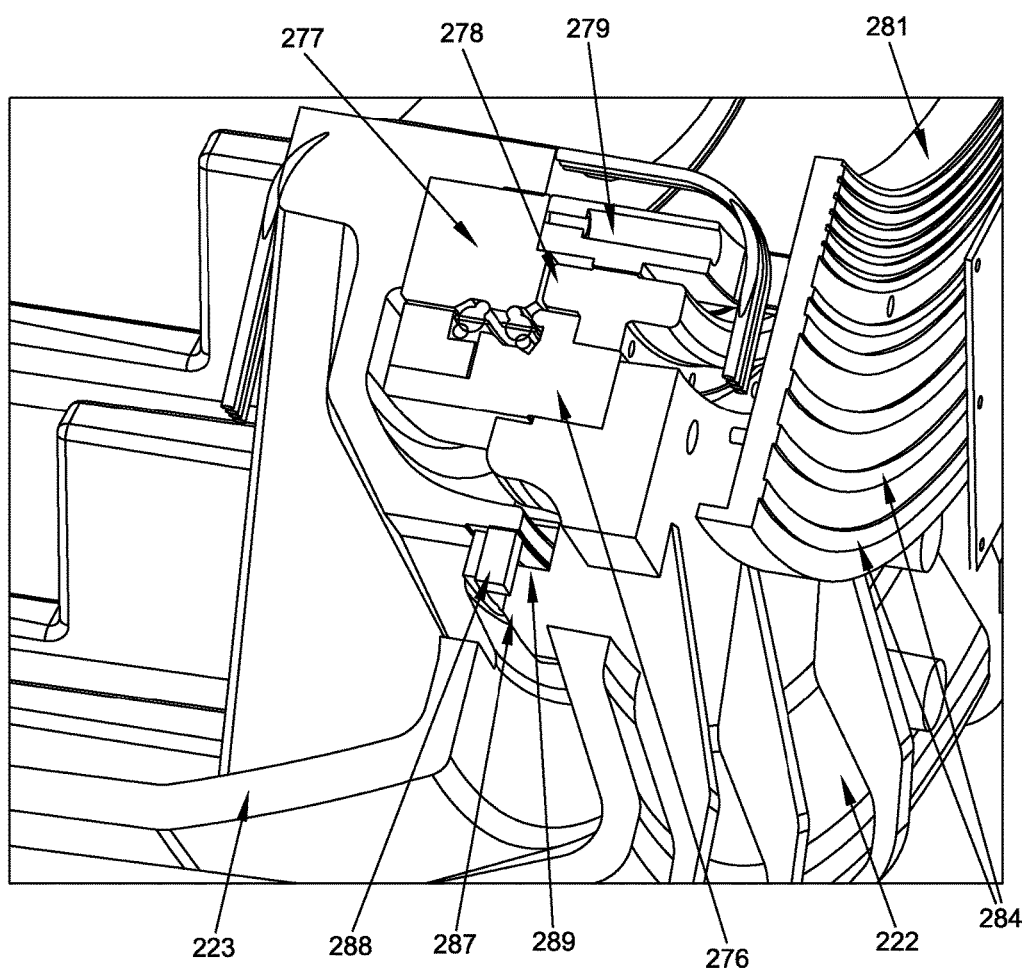
FIGS. 29 and 30 are schematic views showing a novel position sensor formed in accordance with the present invention.
Figure 30:
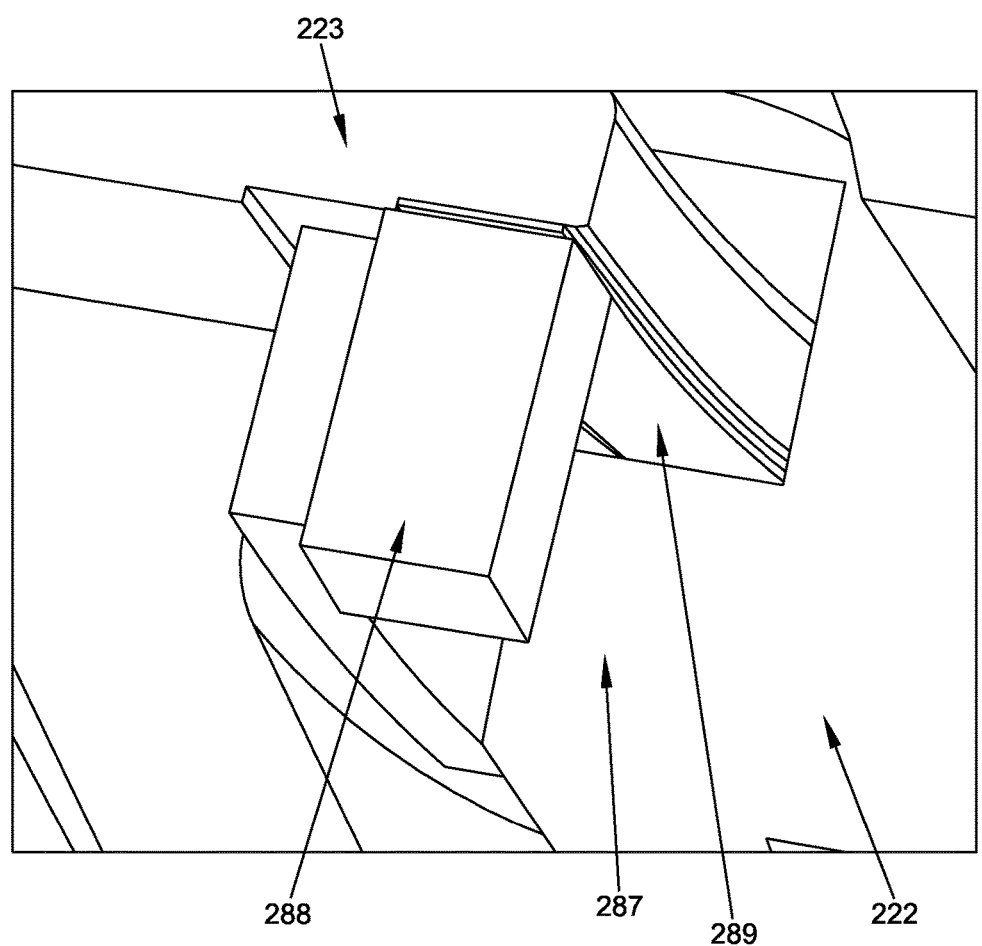

Looking next at FIGS. 29 and 30, if desired, a position sensor 287 may be provided for determining the rotational disposition of rotating cup-shaped disc 223 relative to fixed cup-shaped gantry 222 in real-time. Position sensor 287 preferably comprises a fixed encoder reader 288 and a rotating rotary encoder strip 289. Fixed encoder reader 288 is preferably mounted to fixed cup-shaped gantry 222 and reads rotating rotary encoder strip 289, which is mounted to, and extends circumferentially around, rotating cup-shaped disc 223. Fixed encoder reader 288 may comprise any suitable encoder reader known in the art (e.g., an electrical encoder reader, a magnetic encoder reader, an optical encoder reader, etc.) for pairing with a suitable rotating rotary encoder strip 289.

It should be appreciated that, by mounting fixed encoder reader 288 directly to fixed cup-shaped gantry 222, and by mounting rotating rotary encoder strip 289 directly to rotating cup-shaped disc 223, the absolute rotational disposition of rotating cup-shaped disc 223 can be determined at any point in time. This is a significant improvement over other approaches which typically rely on a "home" marker located on the drive shaft of the motor used to rotate the rotating disc, since reading a single "home" marker on the drive shaft of the motor requires an extrapolation to determine mid-rotation positioning and can lead to inaccuracies if there is any slippage between the drive shaft of the motor and the rotating disc.

Application to Other Types of Scanning Systems

It should be appreciated that the present invention is not limited to use in medical applications or, indeed, to use with CT machines. Thus, for example, the present invention may be used in connection with CT machines used for non-medical applications, e.g., with CT machines used to scan inanimate objects. Furthermore, the present invention may be used with non-CT-type scanning systems. Thus, for example, the present invention may be used in conjunction with SPECT machines, MRI machines, PET machines, X-ray machines, etc., i.e., wherever it is desirable to tilt the scanning machine relative to the patient.

Modifications

It will be appreciated that still further embodiments of the present invention will be apparent to those skilled in the art in view of the present disclosure. It is to be understood that the present invention is by no means limited to the particular constructions herein disclosed and/or shown in the drawings, but also comprises any modifications or equivalents within the scope of the invention.

What is claimed is:

1. An apparatus for scanning a patient, said apparatus comprising:
   a base;
   a torus pivotally mounted to said base, said torus comprising a scanning apparatus;
   a planetary gear comprising a curved lower planet gear mounted to said base, a curved upper planet gear mounted to said torus, and a sun gear disposed between said curved lower planet gear and said curved upper planet gear; and
   a motor for rotating said sun gear;
   wherein rotation of said sun gear causes said sun gear to move longitudinally relative to said curved lower planet gear, and also causes said curved upper planet gear to move longitudinally relative to said sun gear, whereby to move said upper planet gear longitudinally relative to said lower planet gear;
   and further wherein longitudinal movement of said curved upper planet gear relative to said curved lower planet gear tilts said torus relative to said base.

2. The apparatus according to claim 1, wherein said base comprises a carrier movably mounted thereto, wherein said sun gear is mounted to said carrier, and further wherein rotation of said sun gear causes said carrier to move relative to said base.

3. The apparatus according to claim 1, further comprising a brake for preventing said torus from pivoting relative to said base.

4. The apparatus according to claim 3, wherein said brake is mounted to said base, said torus comprises a slot disposed opposite said brake, and further wherein said brake comprises a wedge and an actuator for selectively moving said wedge into and out of said slot.

5. The apparatus according to claim 4, wherein said slot is arcuate.

6. The apparatus according to claim 5, wherein said slot comprises tapered side walls for engagement by said wedge.

7. The apparatus according to claim 1, further comprising a fail-safe brake for preventing said torus from pivoting relative to said base when power is interrupted.

8. The apparatus according to claim 7, wherein said fail-safe brake is mounted to said planetary gear such that when said fail-safe brake is activated, rotation of said sun gear is prevented.

9. A method for scanning a patient, said method comprising:
   providing an apparatus comprising:
      a base;
      a torus pivotally mounted to said base, said torus comprising a scanning apparatus;
      a planetary gear comprising a curved lower planet gear mounted to said base, a curved upper planet gear mounted to said torus, and a sun gear disposed between said curved lower planet gear and said curved upper planet gear; and
      a motor for rotating said sun gear;
      wherein rotation of said sun gear causes said sun gear to move longitudinally relative to said curved lower planet gear, and also causes said curved upper planet gear to move longitudinally relative to said sun gear, whereby to move said upper planet gear longitudinally relative to said lower planet gear;
      and further wherein longitudinal movement of said curved upper planet gear relative to said curved lower planet gear tilts said torus relative to said base;
   tilting said torus relative to said base by rotating said sun gear;
   positioning the patient to be scanned within said torus; and
   scanning the patient.

10. The method according to claim 9, wherein said base comprises a carrier movably mounted thereto, wherein said sun gear is mounted to said carrier, and further wherein rotation of said sun gear causes said carrier to move relative to said base.

11. The method according to claim 9, further comprising a brake for preventing said torus from pivoting relative to said base.

12. The method according to claim 11, wherein said brake is mounted to said base, said torus comprises a slot disposed opposite said brake, and further wherein said brake comprises a wedge and an actuator for selectively moving said wedge into and out of said slot.

13. The method according to claim 12, wherein said slot is arcuate.

14. The method according to claim 13, wherein said slot comprises tapered side walls for engagement by said wedge.

15. The method according to claim 11, further comprising a fail-safe brake for preventing said torus from pivoting relative to said base when power is interrupted.

16. The method according to claim 15, wherein said fail-safe brake is mounted to said planetary gear such that when said fail-safe brake is activated, rotation of said sun gear is prevented.

* * * * *